(12) United States Patent
Shibuya et al.

(10) Patent No.: US 10,566,544 B2
(45) Date of Patent: *Feb. 18, 2020

(54) COMPOUND AND ORGANIC PHOTOELECTRIC DEVICE, IMAGE SENSOR AND ELECTRONIC DEVICE INCLUDING THE SAME

(71) Applicant: Samsung Electronics Co., Ltd., Suwon-si, Gyeonggi-do (KR)

(72) Inventors: Hiromasa Shibuya, Seongnam-si (KR); Tatsuya Imase, Yokohama (JP); Rie Sakurai, Suwon-si (KR); Xavier Bulliard, Seongnam-si (KR); Hyesung Choi, Seoul (KR); Tadao Yagi, Hwaseong-si (KR); Sung Young Yun, Suwon-si (KR); Gae Hwang Lee, Seongnam-si (KR); Kwang Hee Lee, Hwaseong-si (KR); Dong-Seok Leem, Seongnam-si (KR); Yeong Suk Choi, Suwon-si (KR)

(73) Assignee: Samsung Electronics Co., Ltd., Gyeonggi-do (KR)

(*) Notice: Subject to any disclaimer, the term of this patent is extended or adjusted under 35 U.S.C. 154(b) by 0 days.

This patent is subject to a terminal disclaimer.

(21) Appl. No.: 16/297,931

(22) Filed: Mar. 11, 2019

(65) Prior Publication Data

US 2019/0207119 A1 Jul. 4, 2019

Related U.S. Application Data

(62) Division of application No. 15/461,914, filed on Mar. 17, 2017, now Pat. No. 10,276,802.

(30) Foreign Application Priority Data

Apr. 6, 2016 (KR) ........................ 10-2016-0042427

(51) Int. Cl.
| | | |
|---|---|---|
| *C07D 343/00* | (2006.01) | |
| *C09K 11/06* | (2006.01) | |
| *H05B 33/14* | (2006.01) | |
| *H01L 51/50* | (2006.01) | |
| *H01L 51/00* | (2006.01) | |
| *C07D 421/12* | (2006.01) | |
| *C07D 421/14* | (2006.01) | |
| *C07F 11/00* | (2006.01) | |
| *H01L 27/30* | (2006.01) | |
| *H01L 51/42* | (2006.01) | |
| *H01L 51/44* | (2006.01) | |

(52) U.S. Cl.
CPC ........ *H01L 51/0067* (2013.01); *C07D 421/12* (2013.01); *C07D 421/14* (2013.01); *C07F 11/005* (2013.01); *C09K 11/06* (2013.01); *H01L 51/0053* (2013.01); *H01L 51/0058* (2013.01); *H01L 51/0061* (2013.01); *H01L 51/0062* (2013.01); *H05B 33/14* (2013.01); *H01L 27/307* (2013.01); *H01L 51/4253* (2013.01); *H01L 51/442* (2013.01)

(58) Field of Classification Search
CPC ... C07D 343/00; C09K 11/06; H01L 51/5032; H01L 51/5064; H01L 51/0032; H01L 51/5296; H05B 33/14
USPC ................ 540/1; 257/40, E51.008; 313/504; 428/690, 917
See application file for complete search history.

(56) References Cited

U.S. PATENT DOCUMENTS

| | | | |
|---|---|---|---|
| 6,087,258 A | 7/2000 | Simpson et al. | |
| 6,300,612 B1 | 10/2001 | Yu | |
| 6,824,952 B1 | 11/2004 | Minsek et al. | |
| 6,972,431 B2 | 12/2005 | Forrest et al. | |
| 7,129,466 B2 | 10/2006 | Iwasaki | |
| 7,141,863 B1 | 11/2006 | Compaan et al. | |
| 7,973,307 B2 | 7/2011 | Rand et al. | |
| 8,035,708 B2 | 10/2011 | Takizawa et al. | |
| 8,378,339 B2 | 2/2013 | Nomura et al. | |
| 8,426,727 B2 | 4/2013 | Pfeiffer et al. | |
| 8,471,246 B2 | 6/2013 | Suzuki et al. | |
| 8,525,577 B2 | 9/2013 | Yofu et al. | |
| 8,637,860 B2 | 1/2014 | Nomura et al. | |
| 8,704,213 B2 | 4/2014 | Suzuki | |
| 8,704,281 B2 | 4/2014 | Maehara et al. | |
| 8,847,141 B2 | 9/2014 | Fukuzaki et al. | |
| 8,847,208 B2 | 9/2014 | Mitsui et al. | |
| 8,860,016 B2 | 10/2014 | Suzuki | |
| 8,933,438 B2 | 1/2015 | Leem et al. | |
| 8,994,132 B2 | 3/2015 | Mitsui et al. | |
| 9,070,888 B2 | 6/2015 | Leem et al. | |
| 9,543,361 B2 | 1/2017 | Leem et al. | |
| 9,548,463 B2 | 1/2017 | Yagi et al. | |

(Continued)

FOREIGN PATENT DOCUMENTS

| | | |
|---|---|---|
| CN | 104230953 A | 12/2014 |
| DE | 102004014046 A1 | 9/2004 |

(Continued)

OTHER PUBLICATIONS

Advanced Materials (1997), 9(2), 132-135.
Jap. J. Appl. Phys. 46(49), 2007, L1240-L1242.
IEEE Trans. Electron. Dev., 56(11), 2009, 2570.
IDW '09, INP 1-4.
Scientific Reports 5, Article No. 7708 (2015).
Journal of Synthetic Organic Chemistry, Japan, vol. 63 (2005) No. 9 p. 911-920.
The Biophysical Society of Japan, vol. 2, pp. 23-34 (2006).
J. Phys. Chem. A 2013, 117, 9259-9265.

(Continued)

*Primary Examiner* — Venkataraman Balasubramanian
(74) *Attorney, Agent, or Firm* — Harness, Dickey & Pierce, P.L.C.

(57) ABSTRACT

Example embodiments provide a compound of Chemical Formula 1, and an organic photoelectric device, an image sensor, and an electronic device including the same.

31 Claims, 7 Drawing Sheets

(56) References Cited

U.S. PATENT DOCUMENTS

| | | | |
|---|---|---|---|
| 9,941,477 B2* | 4/2018 | Choi | H01L 51/0062 |
| 9,960,362 B2 | 5/2018 | Bulliard et al. | |
| 9,997,718 B2* | 6/2018 | Rie | H01L 51/0071 |
| 10,224,486 B2* | 3/2019 | Yagi | H01L 51/0061 |
| 10,236,461 B2* | 3/2019 | Ro | H01L 27/307 |
| 10,263,042 B2* | 4/2019 | Sakurai | H01L 27/307 |
| 2005/0217722 A1 | 10/2005 | Komatsu et al. | |
| 2006/0076050 A1 | 4/2006 | Williams et al. | |
| 2007/0012955 A1 | 1/2007 | Ihama | |
| 2007/0063156 A1 | 3/2007 | Hayashi | |
| 2007/0090371 A1 | 4/2007 | Drechsel et al. | |
| 2010/0207112 A1 | 8/2010 | Furst et al. | |
| 2011/0012091 A1 | 1/2011 | Forrest et al. | |
| 2011/0074491 A1 | 3/2011 | Yofu et al. | |
| 2012/0126204 A1 | 5/2012 | So et al. | |
| 2012/0266958 A1 | 10/2012 | Aksu et al. | |
| 2012/0313088 A1 | 12/2012 | Yofu et al. | |
| 2013/0062595 A1 | 3/2013 | Park et al. | |
| 2013/0087682 A1 | 4/2013 | Nomura | |
| 2013/0181202 A1 | 7/2013 | Yofu et al. | |
| 2014/0008619 A1 | 1/2014 | Lee et al. | |
| 2014/0054442 A1 | 2/2014 | Huang et al. | |
| 2014/0083496 A1 | 3/2014 | Shibasaki et al. | |
| 2014/0159752 A1 | 6/2014 | Tsai et al. | |
| 2014/0209173 A1 | 7/2014 | Momose | |
| 2014/0319509 A1 | 10/2014 | Hattori et al. | |
| 2015/0053942 A1 | 2/2015 | Kho et al. | |
| 2015/0060775 A1 | 3/2015 | Liang et al. | |
| 2015/0162548 A1 | 6/2015 | Lim et al. | |
| 2015/0228811 A1 | 8/2015 | Hiroi et al. | |
| 2015/0349073 A1 | 12/2015 | Kang | |
| 2016/0013248 A1 | 1/2016 | Sawaki | |
| 2016/0013424 A1 | 1/2016 | Yamamoto et al. | |
| 2016/0020258 A1 | 1/2016 | Park et al. | |
| 2016/0064672 A1 | 3/2016 | Lee et al. | |
| 2016/0099417 A1 | 4/2016 | Sato et al. | |
| 2016/0111561 A1 | 4/2016 | Hsu et al. | |
| 2016/0111651 A1 | 4/2016 | Yun et al. | |
| 2016/0126470 A1 | 5/2016 | Ro et al. | |
| 2016/0149132 A1 | 5/2016 | Lim et al. | |
| 2016/0197281 A1 | 7/2016 | Momose et al. | |
| 2016/0268401 A1 | 9/2016 | Aleksov | |
| 2017/0005142 A1 | 1/2017 | Lee et al. | |
| 2017/0074652 A1 | 3/2017 | Send et al. | |
| 2017/0117424 A1 | 4/2017 | Hiroi et al. | |
| 2017/0294589 A1 | 10/2017 | Shibuya et al. | |
| 2018/0151624 A1 | 5/2018 | Hasegawa et al. | |

FOREIGN PATENT DOCUMENTS

| | | | |
|---|---|---|---|
| EP | 0529162 A1 | 3/1993 | |
| EP | 2317582 A1 | 5/2011 | |
| EP | 3026722 A1 | 6/2016 | |
| JP | H09-311232 A | 12/1997 | |
| JP | 10-91384 A | 4/1998 | |
| JP | 2005-132914 A | 5/2005 | |
| JP | 2006-261172 A | 9/2006 | |
| JP | 2007-234650 A | 9/2007 | |
| JP | 2009-274966 A | 11/2009 | |
| JP | 2011-225544 A | 11/2011 | |
| JP | 2011-253861 A | 12/2011 | |
| JP | 2012-123292 A | 6/2012 | |
| JP | 2012-151761 A | 8/2012 | |
| JP | 2013-040147 A | 2/2013 | |
| JP | 5323025 B2 | 10/2013 | |
| JP | 2014-049559 A | 3/2014 | |
| JP | 2014-210768 A | 11/2014 | |
| JP | 2015-015415 A | 1/2015 | |
| JP | 2015-043362 A | 3/2015 | |
| JP | 2015-700600 A | 4/2015 | |
| JP | 2015-092546 A | 5/2015 | |
| KR | 10-2014-0106767 A | 9/2014 | |
| KR | 10-2015-0066616 A | 6/2015 | |
| KR | 10-2016-0009404 A | 1/2016 | |
| KR | 10-2016-0024686 A | 3/2016 | |
| KR | 10-2016-0052448 A | 5/2016 | |
| KR | 10-2016-0062708 A | 6/2016 | |
| WO | WO-2002/064600 A1 | 8/2002 | |
| WO | WO-2008/191670 A2 | 7/2008 | |
| WO | WO-2010/011658 A2 | 1/2010 | |
| WO | WO-2010038721 A1 | 4/2010 | |
| WO | WO-2014-157238 A1 | 10/2014 | |
| WO | WO-2014/169270 A2 | 10/2014 | |

OTHER PUBLICATIONS

Extended European Search Report dated May 22, 2017, for corresponding European Patent Application No. 17161078.5.

Juha Alakarhu, "Image Sensors and Image Quality in Mobile Phones", International Image Sensor Workshop, 2007, pp. 1-4.

Hokuto Seo et al. "Color Sensors with Three Vertically Stacked Organic Photodetectors". Japanese Journal of Applied Physics, vol. 46, No. 49. The Japan Society of Applied Physics. 2007. pp. L1240-L1242.

I.G. Hill et al., Organic Electronics, "Metal-dependent charge transfer and chemical interaction at interfaces between 3, 4, 9, 10-perylenetetracarboxylic bisimidazole and gold, silver, and magnesium", vol. 1, Issue 1, Dec. 2000, pp. 5-13.

Drechsel J. et al: "Efficient organic solar cells based on a double p-i-n architecture using doped wide-gap transport layers", Applied Physics Letters, AIP Publishing LLC, US, vol. 86, No. 24, Jun. 7, 2005 (Jun. 7, 2005), pp. 244102-244102, XP012065900, ISSN: 0003-6951, DOI: 10.1063/1.1935771.

Marzena Grucela-Zajac et al, "(Photo)physical Properties of New Molecular Glasses End-Capped with Thiophene Rings Composed of Diimide and Imine Units", The Journal of Physical Chemistry, May 21, 2014, pp. 13070-13086, ACS Author Choice.

Gorkem Memisoglu et al., "Highly Efficient Organic UV Photodetectors Based on Polyfluorene and Naphthalenediimide Blends: Effect of Thermal Annealing", 2012, International Journal of Photoenergy vol. 2012, Article ID 936075, 11 pages, Hindawi Publishing Corporation.

Jiří Misek et al., "A Chiral and Colorful Redox Switch: Enhanced p Acidity in Action", 2010, Angew. Chem. Int. Ed. 2010, 49, 7680 -7683, Wiley-VCH Verlag GmbH & Co. KGaA, Weinheim.

European Search Report dated Apr. 26, 2017 issued in corresponding European Application No. 16195944.0.

European Search Report for Application No. 17177002.7 dated Nov. 17, 2017.

European Search Report issued in corresponding European Patent Application No. 17150423.6-1555 dated Aug. 4, 2017.

U.S. Notice of Allowance dated Dec. 20, 2017 issued in co-pending U.S. Appl. No. 15/609,125.

U.S. Office Action dated Feb. 14, 2018 issued in co-pending U.S. Appl. No. 15/272,580.

U.S. Office Action dated Jan. 5, 2018 issued in co-pending U.S. Appl. No. 15/362,964.

U.S. Office Action dated Jun. 1, 2018 issued in co-pending U.S. Appl. No. 15/362,964.

U.S. Office Action dated Jul. 3, 2017 issued in copending U.S. Appl. No. 15/255,649.

U.S. Office Action dated Jan. 29, 218 in co-pending U.S. Appl. No. 15/255,649.

European Office Action for corresponding U.S. Appl. No. 15/362,964 dated Nov. 29, 2016.

European Search Report for corresponding European Application No. 17150423.6-1555 dated Aug. 4, 2017.

European Search Report dated Apr. 26, 2017 issued in corresponding European Application No. 16195944.0-1552.

I.G. Hill et al., Organic Electronics, "Metal-dependent charge transfer and chemical interaction at interfaces between 3,4,9,10-perylenetetracarboxylic bisimidazole and gold, silver and magnesium", Department of Electrical Engineering, Princetion Materials Institute, Feb. 2000, pp. 5-13.

U.S. Office Action dated Jul. 25, 2018 issued in co-pending U.S. Appl. No. 15/272,580.

U.S. Office Action dated Aug. 6, 2018 issued in co-pending U.S. Appl. No. 15/623,801.

(56) References Cited

OTHER PUBLICATIONS

Final Office Action issued for co-pending U.S. Appl. No. 15/255,649 dated Aug. 30, 2018.
Office Action for U.S. Appl. No. 15/623,801 dated Feb. 14, 2019.
Notice of Allowance dated Mar. 28, 2019 issued in co-pending U.S. Appl. No. 15/334,586.

* cited by examiner

COMPOUND AND ORGANIC PHOTOELECTRIC DEVICE, IMAGE SENSOR AND ELECTRONIC DEVICE INCLUDING THE SAME

CROSS-REFERENCE TO RELATED APPLICATION

This application is a divisional application of U.S. application Ser. No. 15/461,914, filed on Mar. 17, 2017, which claims priority to Korean Patent Application No. 10-2016-0042427 filed in the Korean Intellectual Property Office on Apr. 6, 2016, and all the benefits accruing therefrom under 35 U.S.C. § 119. The entire contents of each of the above-referenced applications are incorporated herein by reference.

BACKGROUND

1. Field

Example embodiments relate to a compound and an organic photoelectric device, an image sensor, and an electronic device including the same.

2. Description of the Related Art

A photoelectric device may convert light into an electrical signal using photoelectric effects. A photoelectric device may include a photodiode, a phototransistor, etc. A photoelectric device may be applied to an image sensor, a solar cell, an organic light emitting diode, etc.

An image sensor including a photodiode requires relatively high resolution and thus a smaller pixel. At present, a silicon photodiode is widely used. In some cases, a silicon photodiode exhibits a problem of deteriorated sensitivity because of a relatively small absorption area due to relatively small pixels. Accordingly, an organic material that is capable of replacing silicon has been researched.

An organic material has a relatively high extinction coefficient and selectively absorbs light in a particular wavelength region depending on a molecular structure, and thus may simultaneously replace a photodiode and a color filter and resultantly improve sensitivity and contribute to relatively high integration.

SUMMARY

Example embodiments provide a compound that selectively absorbs light in a green wavelength region.

Example embodiments also provide an organic photoelectric device capable of selectively absorbing light in a green wavelength region and improving efficiency.

Example embodiments also provide an image sensor including the organic photoelectric device.

Example embodiments also provide an electronic device including the image sensor.

According to example embodiments, a compound represented by Chemical Formula 1.

[Chemical Formula 1]

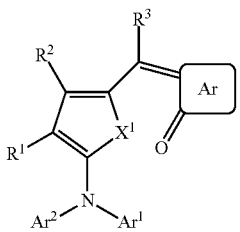

In Chemical Formula 1,

Ar is selected from a substituted or unsubstituted 5-membered aromatic ring, a substituted or unsubstituted 6-membered aromatic ring, and a condensed ring of two or more of the foregoing rings, $X^1$ is selected from Se, Te, O, $NR^a$, $S(=O)$, $S(=O)_2$, and $SiR^bR^c$, wherein each of $R^a$, $R^b$, and $R^c$ are selected from hydrogen and a substituted or unsubstituted $C_1$ to $C_{10}$ alkyl group, each of $R^1$ to $R^3$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, and each of $Ar^1$ and $Ar^2$ are independently selected from a substituted or unsubstituted $C_6$ to $C_{30}$ aryl group, and a substituted or unsubstituted $C_3$ to $C_{30}$ heteroaryl group, provided that at least one of $Ar^1$ and $Ar^2$ is a heteroaryl group including at least one nitrogen (N) at an ortho position with respect to a bond with the nitrogen (N).

In Chemical Formula 1, at least one of $Ar^1$ and $Ar^2$ may selected from a substituted or unsubstituted pyrrolyl group, a substituted or unsubstituted prazolyl group, a substituted or unsubstituted midazolyl group, a substituted or unsubstituted oxazolyl group, a substituted or unsubstituted isoxazolyl group, a substituted or unsubstituted thiazolyl group, a substituted or unsubstituted isothiazolyl group, a substituted or unsubstituted pyridinyl group, a substituted or unsubstituted pyridazinyl group, a substituted or unsubstituted pyrimidinyl group, a substituted or unsubstituted pyrazinyl group, a substituted or unsubstituted indolyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, a substituted or unsubstituted pyridopyridazinyl group, a substituted or unsubstituted thienyl group, a substituted or unsubstituted benzothienyl group, a substituted or unsubstituted selenophenyl group, and a substituted or unsubstituted benzoselenophenyl group, and the functional groups may include at least one nitrogen (N) at an ortho position with respect to a bond with the nitrogen (N).

The compound represented by Chemical Formula 1 may be represented by Chemical Formula 2.

[Chemical Formula 2]

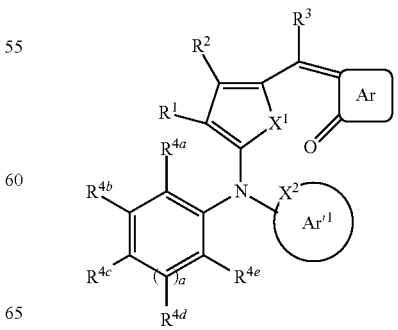

In Chemical Formula 2,

Ar is selected from a substituted or unsubstituted 5-membered aromatic ring, a substituted or unsubstituted 6-membered aromatic ring, and a condensed ring of two or more of the foregoing rings, $X^1$ is selected from Se, Te, O, $NR^a$, $S(=O)$, $S(=O)_2$, and $SiR^bR^c$, wherein $R^a$, $R^b$, and $R^c$ are selected from hydrogen and a substituted or unsubstituted $C_1$ to $C_{10}$ alkyl group, each of $R^1$ to $R^3$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, each of $R^{4a}$ to $R^{4e}$ are independently selected from hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof or optionally two adjacent groups of $R^{4a}$ to $R^{4e}$ are linked with each other to provide a 5-membered aromatic ring or a 6-membered aromatic ring, a is an integer of 0 or 1, $X^2$ is nitrogen (N), and $Ar'^1$ is a heteroaryl group including at least one nitrogen (N) at an ortho position with respect to a bond with the nitrogen (N) of Chemical Formula 2.

In Chemical Formula 2, $Ar'^1$ may be selected from a substituted or unsubstituted pyrrolyl group, a substituted or unsubstituted pyrazolyl group, a substituted or unsubstituted imidazolyl group, a substituted or unsubstituted oxazolyl group, a substituted or unsubstituted isoxazolyl group, a substituted or unsubstituted thiazolyl group, a substituted or unsubstituted isothiazolyl group, a substituted or unsubstituted pyridinyl group, a substituted or unsubstituted pyridazinyl group, a substituted or unsubstituted pyrimidinyl group, a substituted or unsubstituted pyrazinyl group, a substituted or unsubstituted indolyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, a substituted or unsubstituted pyridopyridazinyl group, a substituted or unsubstituted thienyl group, a substituted or unsubstituted benzothienyl group, a substituted or unsubstituted selenophenyl group, and a substituted or unsubstituted benzoselenophenyl group, and the functional groups may include at least one nitrogen (N) at an ortho position with respect to a bond with the nitrogen (N).

The compound represented by Chemical Formula 1 may be represented by one of Chemical Formulae 3-1 to 3-6.

[Chemical Formula 3-1]

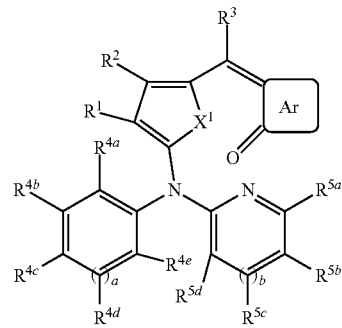

[Chemical Formula 3-2]

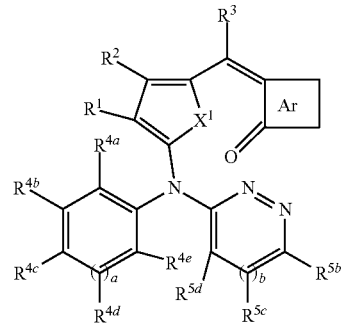

[Chemical Formula 3-3]

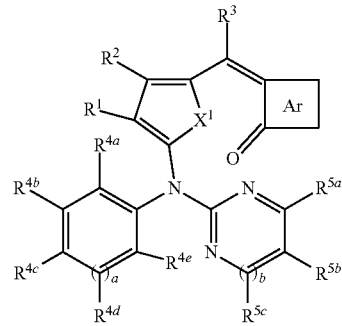

[Chemical Formula 3-4]

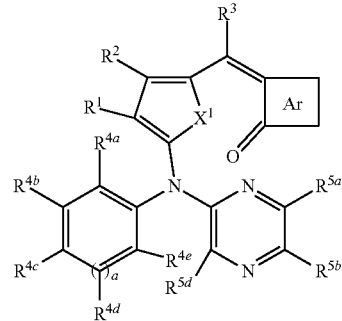

-continued

[Chemical Formula 3-5]

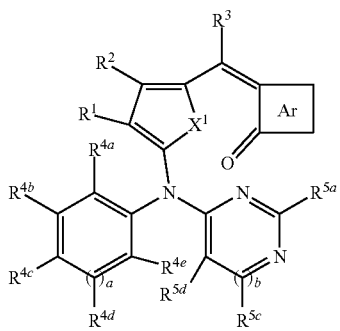

[Chemical Formula 3-6]

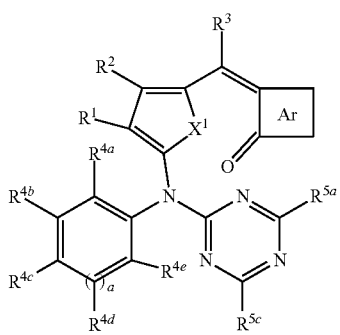

In Chemical Formulae 3-1 to 3-6,

Ar is selected from a substituted or unsubstituted 5-membered aromatic ring, a substituted or unsubstituted 6-membered aromatic ring, and a condensed ring of two or more of the foregoing rings, $X^1$ is selected from Se, Te, O, $NR^a$, S(=O), S(=O)$_2$, and $SiR^bR^c$, wherein each of $R^a$, $R^b$, and $R^c$ are selected from hydrogen and a substituted or unsubstituted $C_1$ to $C_{10}$ alkyl group, each of $R^1$ to $R^3$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, each of $R^{4a}$ to $R^{4e}$ or $R^{5a}$ to $R^{5d}$ are independently selected from hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, or optionally two adjacent groups of $R^{4a}$ to $R^{4e}$ are linked with each other to provide a 5-membered aromatic ring or a 6-membered aromatic ring and optionally two adjacent groups of $R^{5a}$ to $R^{5d}$ are linked with each other to provide a 5-membered aromatic ring or a 6-membered aromatic ring, and each of a and b are independently an integer of 0 or 1.

In Chemical Formulae 1, 2, and 3-1 to 3-6, a ring group represented by Ar and bound to a methine group may be represented by Chemical Formula 4.

[Chemical Formula 4]

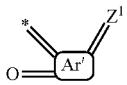

In Chemical Formula 4,

Ar' is selected from a substituted or unsubstituted 5-membered aromatic ring, a substituted or unsubstituted 6-membered aromatic ring, and a condensed ring of two or more of the foregoing rings, and $Z^1$ is O or $CR^bR^c$, wherein each of $R^b$ and $R^c$ are independently selected from hydrogen, a substituted or unsubstituted $C_1$ to $C_{10}$ alkyl group, a cyano group, or a cyano-containing group, provided that at least one of $R^b$ and $R^c$ is a cyano group or a cyano-containing group.

In Chemical Formulae 1, 2, and 3-1 to 3-6, the ring group represented by Ar and bound to a methine group may be a ring group represented by one of Chemical Formulae 5-1 to 5-4.

[Chemical Formula 5-1]

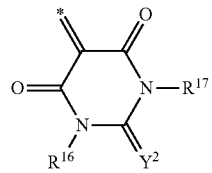

In Chemical Formula 5-1, $Z^1$ is O or $CR^bR^c$, wherein each of $R^b$ and $R^c$ are independently selected from hydrogen, a substituted or unsubstituted $C_1$ to $C_{10}$ alkyl group, a cyano group, or a cyano-containing group, provided that at least one of $R^b$ and $R^c$ is a cyano group or a cyano-containing group, $Y^1$ is selected from N and $CR^d$, wherein $R^d$ is selected from hydrogen and a substituted or unsubstituted $C_1$ to $C_{10}$ alkyl group, each of $R^{11}$, $R^{12}$, $R^{13}$, $R^{14}$, and $R^{15}$ is hydrogen, a substituted or unsubstituted $C_1$ to $C_{30}$ alkyl group, a substituted or unsubstituted $C_6$ to $C_{30}$ aryl group, a substituted or unsubstituted $C_4$ to $C_{30}$ heteroaryl group, a halogen, a cyano group (—CN), a cyano-containing group, and a combination thereof, or $R^{12}$ and $R^{13}$ are independently linked with each other to provide an aromatic ring and $R^{14}$ and $R^{15}$ are independently linked with each other to provide an aromatic ring, m1 is 0 or 1, and n is 0 or 1.

[Chemical Formula 5-2]

In Chemical Formula 5-2, $Y^2$ is selected from O, S, Se, Te, and $C(R^e)(CN)$, wherein $R^e$ is selected from hydrogen, a cyano group (—CN), and a $C_1$ to $C_{10}$ alkyl group, and each of $R^{16}$ and $R^{17}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_4$ to $C_{30}$ heteroaryl group, a halogen, a cyano group (—CN), and a combination thereof.

[Chemical Formula 5-3]

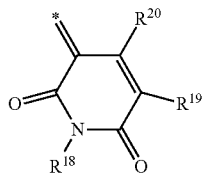

In Chemical Formula 5-3, each of $R^{18}$ to $R^{20}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_4$ to $C_{30}$ heteroaryl group, a halogen, a cyano group (—CN), a cyano-containing group, and a combination thereof.

[Chemical Formula 5-4]

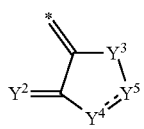

In Chemical Formula 5-4, $Y^2$ is selected from O, S, Se, Te, and $C(R^e)(CN)$ wherein $R^e$ is selected from hydrogen, a cyano group (—CN), and a $C_1$ to $C_{10}$ alkyl group, $Y^3$ is selected from O, S, Se, and Te, $Y^4$ is N or $NR^f$, $Y^5$ is selected from $CR^g$, C=O, C=S, $C=(CR^h)(CN)$, and Chemical Formula 5-4, at least one of $Y^2$ and $Y^5$ is C=O, each of $R^f$, $R^g$, and $R^h$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted C4 to $C_{30}$ heteroaryl group, a halogen, a cyano group (—CN), a cyano-containing group, and a combination thereof, and optionally $Y^4$ and $Y^5$ are linked with each other to provide a fused ring with a $Y^4$-$Y^5$-containing pentagonal ring of Chemical Formula 5-4.

The compound may be a compound represented by one of Chemical Formulae 6-1 to 6-4.

[Chemical Formula 6-1]

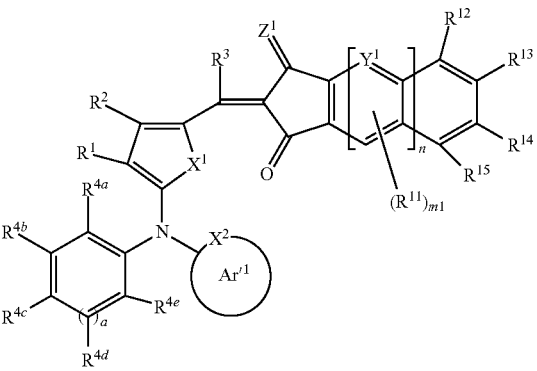

In Chemical Formula 6-1, $X^1$ is selected from Se, Te, O, $NR^a$, S(=O), S(=O)$_2$, and $SiR^bR^c$, wherein each of $R^a$, $R^b$, and $R^c$ are selected from hydrogen and a substituted or unsubstituted $C_1$ to $C_{10}$ alkyl group, each of $R^1$ to $R^3$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, $Z^1$ is O or $CR^bR^c$, wherein each of $R^b$ and $R^c$ are independently selected from hydrogen, a substituted or unsubstituted $C_1$ to $C_{10}$ alkyl group, a cyano group, or a cyano-containing group, provided that at least one of $R^b$ and $R^c$ is a cyano group or a cyano-containing group, $Y^1$ is selected from N and $CR^d$, wherein $R^d$ is selected from hydrogen and a substituted or unsubstituted $C_1$ to $C_{10}$ alkyl group, each of $R^{11}$, $R^{12}$, $R^{13}$, $R^{14}$, and $R^{15}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_4$ to $C_{30}$ heteroaryl group, a halogen, a cyano group (—CN), a cyano-containing group, and a combination thereof or $R^{12}$ and $R^{13}$ are independently linked with each other to provide an aromatic ring and $R^{14}$ and $R^{15}$ are independently linked with each other to provide an aromatic ring, m1 is 0 or 1, n is 0 or 1, each of $R^{4a}$ to $R^{4e}$ are independently selected from hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, or optionally two adjacent groups of $R^{4a}$ to $R^{4e}$ are linked with each other to provide a 5-membered aromatic ring or a 6-membered aromatic ring, a is an integer of 0 or 1, $X^2$ is nitrogen (N), and $Ar'^1$ is heteroaryl group including at least one nitrogen (N) at an ortho position with respect to a bond with the nitrogen (N).

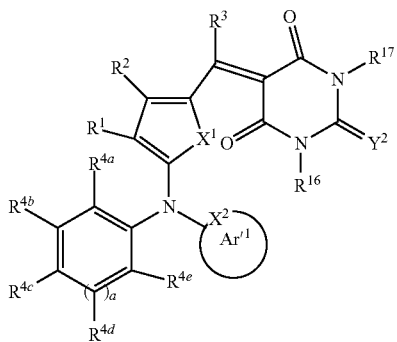

[Chemical Formula 6-2]

In Chemical Formula 6-2, $X^1$ is selected from Se, Te, O, $NR^a$, $S(=O)$, $S(=O)_2$, and $SiR^bR^c$, wherein each of $R^a$, $R^b$, and $R^c$ are selected from hydrogen and a substituted or unsubstituted $C_1$ to $C_{10}$ alkyl group, $Y^2$ is selected from O, S, Se, Te, and $C(R^e)(CN)$ wherein $R^e$ is selected from hydrogen, a cyano group (—CN), and a $C_1$ to $C_{10}$ alkyl group, each of $R^1$, $R^2$, $R^3$, $R^{16}$, and $R^{17}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_4$ to $C_{30}$ heteroaryl group, a halogen, a cyano group (—CN), a cyano-containing group, and a combination thereof, each of $R^{4a}$ to $R^{4e}$ are independently selected from hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, or optionally two adjacent groups of $R^{4a}$ to $R^{4e}$ are linked with each other to provide a 5-membered aromatic ring or a 6-membered aromatic ring, a is an integer of 0 or 1, $X^2$ is nitrogen (N), and $Ar^{r1}$ is heteroaryl group including at least one nitrogen (N) at an ortho position with respect to a bond with the nitrogen (N).

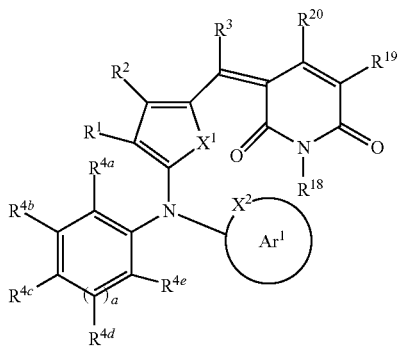

[Chemical Formula 6-3]

In Chemical Formula 6-3, $X^1$ is selected from Se, Te, O, $NR^a$, $S(=O)$, $S(=O)_2$, and $SiR^bR^c$, wherein each of $R^a$, $R^b$, and $R^c$ are selected from hydrogen and a substituted or unsubstituted $C_1$ to $C_{10}$ alkyl group, each of $R^1$, $R^2$, $R^3$, $R^{18}$, $R^{19}$, and $R^{20}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_4$ to $C_{30}$ heteroaryl group, a halogen, a cyano group (—CN), a cyano-containing group, and a combination thereof, each of $R^{4a}$ to $R^{4e}$ are independently selected from hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, or optionally two adjacent groups of $R^{4a}$ to $R^{4e}$ are linked with each other to provide a 5-membered aromatic ring or a 6-membered aromatic ring, a is an integer of 0 or 1, $X^2$ is nitrogen (N), and $Ar^{r1}$ is heteroaryl group including at least one nitrogen (N) at an ortho position with respect to a bond with the nitrogen (N).

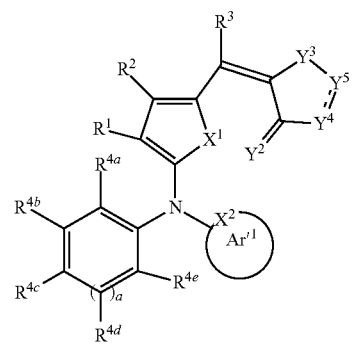

[Chemical Formula 6-4]

$X^1$ is selected from Se, Te, O, $NR^a$, $S(=O)$, $S(=O)_2$, and $SiR^bR^c$, wherein each of $R^a$, $R^b$, and $R^c$ are selected from hydrogen and a substituted or unsubstituted $C_1$ to $C_{10}$ alkyl group, $Y^2$ is selected from O, S, Se, Te, and $C(R^e)(CN)$ wherein $R^e$ is selected from hydrogen, a cyano group (—CN), and a $C_1$ to $C_{10}$ alkyl group, $Y^3$ is selected from O, S, Se, and Te, $Y^4$ is N or $NR^f$, $Y^5$ is selected from $CR^g$, $C=O$, $C=S$, $C=(CR^h)(CN)$, and Chemical Formula 5-4, at least one of $Y^2$ and $Y^5$ is $C=O$, each of $R^1$, $R^2$, $R^3$, $R^f$, $R^g$, and $R^h$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_4$ to $C_{30}$ heteroaryl group, a halogen, a cyano group (—CN), a cyano-containing group, and a combination thereof, optionally $Y^4$ and $Y^5$ are linked with each other to provide a fused ring with a $Y^4$-$Y^5$-containing pentagonal ring of Chemical Formula 5-4, each of $R^{4a}$ to $R^{4e}$ are independently selected from hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, or optionally two adjacent groups of $R^{4a}$ to $R^{4e}$ are linked with each other to provide a 5-membered aromatic ring or a 6-membered aromatic ring, a is an integer of 0 or 1, $X^2$ is nitrogen (N), and $Ar^1$ is heteroaryl group including at least one nitrogen (N) at an ortho position with respect to a bond with the nitrogen (N).

The compound may have a maximum absorption wavelength (λmax) in a wavelength region of greater than or equal to about 510 nm and less than about 560 nm, for example about 520 nm to about 555 nm in a thin film state.

The compound may exhibit a light absorption curve having a full width at half maximum (FWHM) of about 50 nm to about 110 nm, in a thin film state.

According to example embodiments, an organic photoelectric device includes a first electrode and a second electrode facing each other and an active layer between the first electrode and the second electrode and including the compound represented by Chemical Formula 1.

The compound may be a compound represented by Chemical Formula 2 or Chemical Formula 3.

The ring group represented by Ar and bound to a methine group may be represented by Chemical Formula 4.

The active layer may have a maximum absorption wavelength ($\lambda_{max}$) in a wavelength region of greater than or equal to about 510 nm and less than about 560 nm, for example about 520 nm to about 555 nm.

The active layer may exhibit a light absorption curve having a full width at half maximum (FWHM) of about 50 nm to about 110 nm.

The active layer may have an absorption coefficient of greater than or equal to about $5.5 \times 10^4$ $cm^{-1}$, for example about $5.8 \times 10^4$ $cm^{-1}$ to about $10 \times 10^4$ $cm^{-1}$ when including the compound of Chemical Formula 1 and C60 in a volume ratio of about 0.9:1 to about 1.1:1.

According to example embodiments, an image sensor includes the organic photoelectric device.

The image sensor may include a semiconductor substrate integrated with a plurality of first photo-sensing devices configured to sense light in a blue wavelength region and a plurality of second photo-sensing devices configured to sense light in a red wavelength region, and the organic photoelectric device on the semiconductor substrate and selectively sensing light in a green wavelength region.

The first photo-sensing device and the second photo-sensing device may be stacked in a vertical direction in the semiconductor substrate.

The image sensor may further include a color filter layer between the semiconductor substrate and the organic photoelectric device, and including a blue filter configured to selectively absorb light in a blue wavelength region and a red filter selectively absorbing light in a red wavelength region.

The image sensor may include a green photoelectric device of the organic photoelectric device, a blue photoelectric device configured to selectively absorb light in a blue wavelength region, and a red photoelectric device configured to selectively absorb light in a red wavelength region that are stacked.

The image sensor may have a color difference (ΔE*ab) of less than about 4.0.

According to example embodiments, an electronic device includes the image sensor.

DETAILED DESCRIPTION

Figure 1:
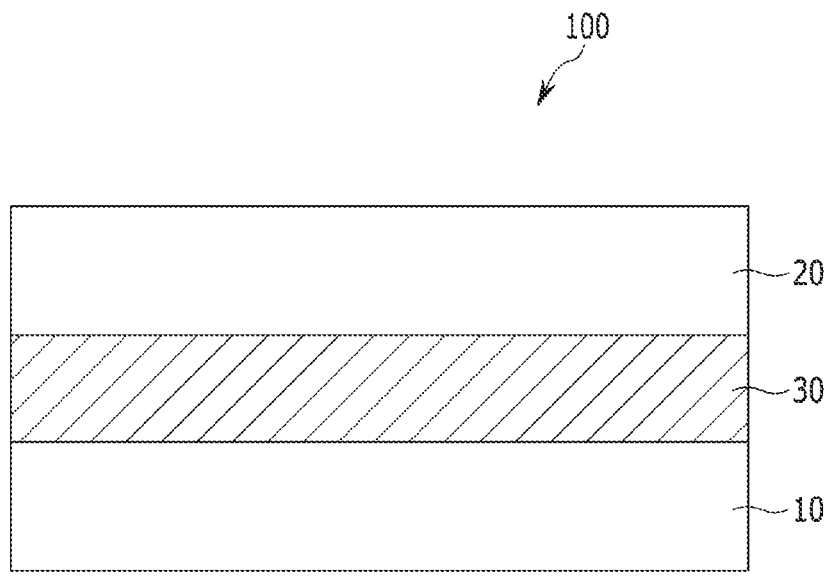
FIG. 1 is a cross-sectional view showing an organic photoelectric device according to example embodiments.

Example embodiments will hereinafter be described in detail, and may be easily performed by those who have common knowledge in the related art. However, this disclosure may be embodied in many different forms and is not to be construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numerals throughout the specification.

As used herein, when specific definition is not otherwise provided, the term "substituted" refers to one substituted with a substituent selected from a halogen atom (F, Cl, Br or I), a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, phosphoric acid group or a salt thereof, a $C_1$ to $C_{20}$ alkyl group, a $C_1$ to $C_{20}$ alkoxy group, a $C_2$ to $C_{20}$ alkenyl group, a $C_2$ to $C_{20}$ alkynyl group, a $C_6$ to $C_{30}$ aryl group, a $C_7$ to $C_{30}$ arylalkyl group, a $C_2$ to $C_{20}$ heteroaryl group, a $C_3$ to $C_{20}$ heteroarylalkyl group, a $C_3$ to $C_{30}$ cycloalkyl group, a $C_3$ to $C_{15}$ cycloalkenyl group, a $C_6$ to $C_{015}$ cycloalkynyl group, a $C_2$ to $C_{20}$ heterocycloalkyl group, and a combination thereof, instead of hydrogen of a compound.

As used herein, when specific definition is not otherwise provided, the term "hetero" refers to one including 1 to 3 heteroatoms selected from N, O, S, P, and Si.

As used herein, the term "alkyl group" for example refers to a methyl group, an ethyl group, a propyl group, an isopropyl group, a n-butyl group, an isobutyl group, a t-butyl group, a pentyl group, a hexyl group, etc.

As used herein, the term "cycloalkyl group" for example refers to a cyclopropyl group, a cyclobutyl group, a cyclopentyl group, a cyclohexyl group, etc.

As used herein, the term "aryl group" refers to a substituent including all element of the cycle having p-orbitals which form conjugation, and may be a monocyclic, polycyclic or fused ring polycyclic (i.e., rings sharing adjacent pairs of carbon atoms) functional group.

As used herein, when a definition is not otherwise provided, the term "cyano-containing group" refers to a monovalent group such as a $C_1$ to $C_{30}$ alkyl group, a C2 to $C_{30}$ alkenyl group, or a C2 to $C_{30}$ alkynyl group where at least one hydrogen is substituted with a cyano group. The cyano-containing group also refers to a divalent group such as a dicyanoalkenyl group represented by $=CR^{x'}-(CR^xR^y)_p-CR^{y'}(CN)_2$ wherein each of $R^x$, $R^y$, $R^{x'}$, and $R^{y'}$ are independently hydrogen or a $C_1$ to $C_{10}$ alkyl group and p is an integer of 0 to 10. Specific examples of the cyano-containing group may be a dicyanomethyl group, a dicyanovinyl group, a cyanoethynyl group, etc.

As used herein, when a definition is not otherwise provided, the term "combination thereof" refers to at least two substituents bound to each other by a single bond or a $C_1$ to $C_{10}$ alkylene group, or at least two fused substituents.

As used herein, the term "5-membered aromatic ring" refers to a 5-membered cyclic group (e.g., $C_5$ aryl group) having a conjugation structure or a 5-membered heterocyclic group (e.g., $C_2$ to $C_4$ heteroaryl group) having a conjugation structure. As used herein, the term "6-membered aromatic ring" refers to a 6-membered cyclic group (e.g., $C_6$ aryl group) having a conjugation structure or a 6-membered heterocyclic group (e.g., $C_2$ to $C_5$ heteroaryl group) having a conjugation structure, but is not limited thereto. The aromatic ring may include the 5-membered aromatic ring or the 6-membered aromatic ring, but is not limited thereto.

Hereinafter, a compound according to example embodiments is described. The compound is represented by Chemical Formula 1.

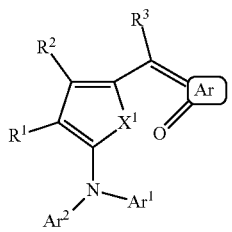

[Chemical Formula 1]

In Chemical Formula 1,

Ar is selected from a substituted or unsubstituted 5-membered aromatic ring, a substituted or unsubstituted 6-membered aromatic ring, and a condensed ring of two or more of the foregoing rings, $X^1$ is selected from Se, Te, O, $NR^a$, $S(=O)$, $S(=O)_2$, and $SiR^bR^c$, wherein each of $R^a$, $R^b$, and $R^c$ are selected from hydrogen and a substituted or unsubstituted $C_1$ to $C_{10}$ alkyl group, each of $R^1$ to $R^3$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted C6 to $C_{30}$ aryl group, a substituted or unsubstituted $C_3$ to $C_{30}$ heteroaryl group, a halogen, a cyano group (—CN), a cyano-containing group, and a combination thereof, each of $Ar^1$ and $Ar^2$ are independently selected from a substituted or unsubstituted C6 to $C_{30}$ aryl group, and a substituted or unsubstituted $C_3$ to $C_{30}$ heteroaryl group, provided that at least one of $Ar^1$ and $Ar^2$ is a heteroaryl group including at least one nitrogen (N) at an ortho position with respect to a bond with the nitrogen (N) of Chemical Formula 1.

The compound represented by Chemical Formula 1 includes electron donor moiety of aryl amine (—N($Ar^1$)($Ar^2$)), a linker including an $X^1$-containing 5-membered ring and a methine group, and an electron acceptor moiety represented by Ar.

Each of $Ar^1$ and $Ar^2$ are a substituted or unsubstituted $C_6$ to $C_{30}$ aryl group or a substituted or unsubstituted $C_3$ to $C_{30}$ heteroaryl group, wherein aromatic rings are present alone or fused together, specifically, a substituted or unsubstituted $C_6$ to $C_{20}$ aryl group, and for example, a substituted or unsubstituted $C_8$ to $C_{20}$ aryl group or a substituted or unsubstituted $C_3$ to $C_{20}$ heteroaryl group. In other words, a single bond between the aromatic rings or a conjugation structure of the aromatic groups connected through another linking group is broken, failing in providing a sufficient conjugation length. In addition, when $Ar^1$ and $Ar^2$ are not the aromatic groups but alkyl groups or connected each other and form a N-containing aliphatic cyclic group, a light absorption curved line has so wide a full width at half maximum (FWHM) that absorption selectivity of a green wavelength region may be deteriorated.

At least either one of $Ar^1$ and $Ar^2$ is a heteroaryl group including at least one nitrogen (N) at an ortho position with respect to a bond with the nitrogen (N) of Chemical Formula 1. At least one nitrogen (N) atom at the ortho position with respect to a bond with the nitrogen (N) may increase an intramolecular interaction between $X^1$ present in the linker and oxygen (O) of a carbonyl group present in the electron acceptor moiety and thus improve absorption intensity at a particular wavelength. When the heteroatom is present at a meta or para position with respect to a bond with the nitrogen (N), the intramolecular interaction may not be sufficient, and thus sufficient absorbance may not be obtained.

In example embodiments, at least one of $Ar^1$ and $Ar^2$ may be a substituted or unsubstituted pyrrolyl group, a substituted or unsubstituted prazolyl group, a substituted or unsubstituted midazolyl group, a substituted or unsubstituted oxazolyl group, a substituted or unsubstituted isoxazolyl group, a substituted or unsubstituted thiazolyl group, a substituted or unsubstituted isothiazolyl group, a substituted or unsubstituted pyridinyl group, a substituted or unsubstituted pyridazinyl group, a substituted or unsubstituted pyrimidinyl group, a substituted or unsubstituted pyrazinyl group, a substituted or unsubstituted indolyl group, a substituted or unsubstituted a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, a substituted or unsubstituted pyridopyridazinyl group, a substituted or unsubstituted thienyl group, a substituted or unsubstituted benzothienyl group, a substituted or unsubstituted selenophenyl group, and a substituted or unsubstituted benzoselenophenyl group, and the functional groups may include at least one nitrogen (N) at an ortho position with respect to a bond with the nitrogen (N).

In example embodiments, one of $Ar^1$ and $Ar^2$ may be a substituted or unsubstituted phenyl group or a substituted or unsubstituted naphthyl group, and the other of $Ar^1$ and $Ar^2$ may be a substituted or unsubstituted pyrrolyl group, a substituted or unsubstituted pyrazolyl group, a substituted or unsubstituted imidazolyl group, a substituted or unsubstituted oxazolyl group, a substituted or unsubstituted isoxazolyl group, a substituted or unsubstituted thiazolyl group, a substituted or unsubstituted isothiazolyl group, a substituted or unsubstituted pyridinyl group, a substituted or unsubstituted pyridazinyl group, a substituted or unsubstituted pyrimidinyl group, a substituted or unsubstituted pyrazinyl group, a substituted or unsubstituted indolyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, a substituted or unsubstituted pyridopyridazinyl group, a substituted or unsubstituted thienyl group, a substituted or unsubstituted benzothienyl group, a substituted or unsubstituted selenophenyl group, and a substituted or unsubstituted benzoselenophenyl group, and the functional groups may include at least one nitrogen (N) at an ortho position with respect to a bond with the nitrogen (N).

The compound represented by Chemical Formula 1 may be represented by Chemical Formula 2.

[Chemical Formula 2]

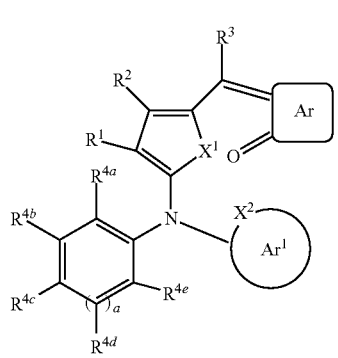

In Chemical Formula 2,

Ar is selected from a substituted or unsubstituted 5-membered aromatic ring, a substituted or unsubstituted 6-membered aromatic ring, and a condensed ring of two or more of the foregoing rings, $X^1$ is selected from Se, Te, O, $NR^a$, $S(=O)$, $S(=O)_2$, and $SiR^bR^c$, wherein each of $R^a$, $R^b$, and $R^c$ are selected from hydrogen and a substituted or unsubstituted $C_1$ to $C_{10}$ alkyl group, each of $R^1$ to $R^3$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, each of $R^{4a}$ to $R^{4e}$ are independently selected from hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, or optionally two adjacent groups of $R^{4a}$ to $R^{4e}$ are linked with each other to provide a 5-membered aromatic ring or a 6-membered aromatic ring, a is an integer of 0 or 1, $X^2$ is nitrogen (N), and $Ar^{r1}$ is heteroaryl group including at least one nitrogen (N) at an ortho position with respect to a bond with the nitrogen (N).

In Chemical Formula 2, $Ar^{r1}$ may be selected from a substituted or unsubstituted pyrrolyl group, a substituted or unsubstituted pyrazolyl group, a substituted or unsubstituted imidazolyl group, a substituted or unsubstituted oxazolyl group, a substituted or unsubstituted isoxazolyl group, a substituted or unsubstituted thiazolyl group, a substituted or unsubstituted isothiazolyl group, a substituted or unsubstituted pyridinyl group, a substituted or unsubstituted pyridazinyl group, a substituted or unsubstituted pyrimidinyl group, a substituted or unsubstituted pyrazinyl group, a substituted or unsubstituted indolyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, a substituted or unsubstituted pyridopyridazinyl group, a substituted or unsubstituted thienyl group, a substituted or unsubstituted benzothienyl group, a substituted or unsubstituted selenophenyl group, and a substituted or unsubstituted benzoselenophenyl group.

The compound represented by Chemical Formula 1 may be represented by one of Chemical Formulae 3-1 to 3-6.

[Chemical Formula 3-1]

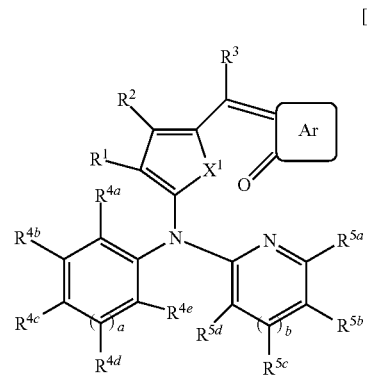

[Chemical Formula 3-2]

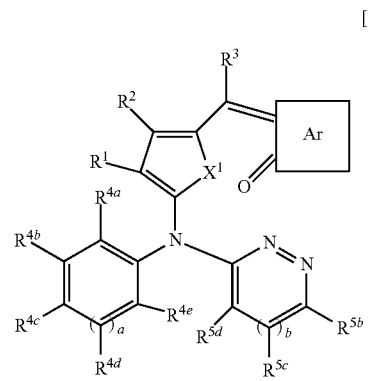

[Chemical Formula 3-3]

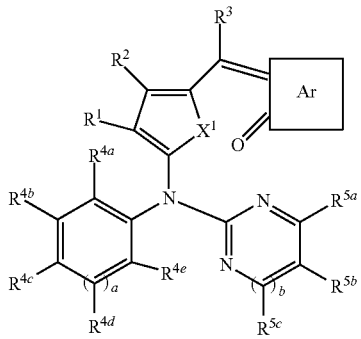

[Chemical Formula 3-4]

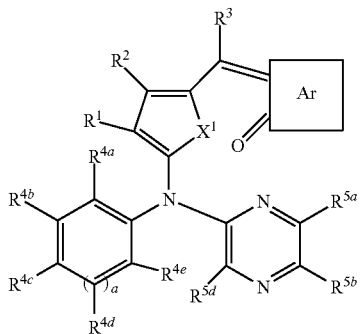

[Chemical Formula 3-5]

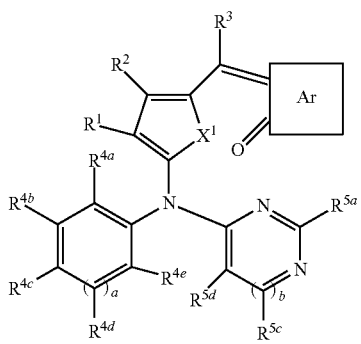

[Chemical Formula 3-6]

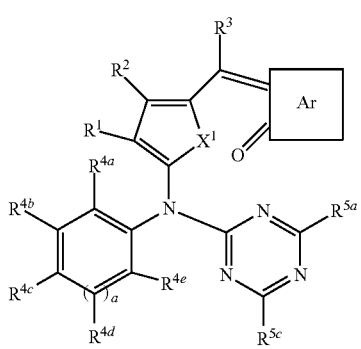

In Chemical Formulae 3-1 to 3-6,

Ar is selected from a substituted or unsubstituted 5-membered aromatic ring, a substituted or unsubstituted 6-membered aromatic ring, and a condensed ring of two or more of the foregoing rings, $X^1$ is selected from Se, Te, O, $NR^a$, $S(=O)$, $S(=O)_2$, and $SiR^bR^c$, wherein each of $R^a$, $R^b$, and $R^c$ are selected from hydrogen and a substituted or unsubstituted $C_1$ to $C_{10}$ alkyl group, each of $R^1$ to $R^3$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, each of $R^{4a}$ to $R^{4e}$ or $R^{5a}$ to $R^{5d}$ are independently selected from hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, or optionally two adjacent groups of $R^{4a}$ to $R^{4e}$ are linked with each other to provide a 5-membered aromatic ring or a 6-membered aromatic ring and optionally two adjacent groups of $R^{5a}$ to $R^{5d}$ are linked with each other to provide a 5-membered aromatic ring or a 6-membered aromatic ring, and each of a and b are independently an integer of 0 or 1.

In Chemical Formula 1, a Chemical Formula 2, and Chemical Formulae 3-1 to 3-6, the ring group represented by Ar is an electron acceptor moiety that includes at least one carbonyl group.

For example, in Chemical Formula 1, Chemical Formula 2, and Chemical Formulae 3-1 to 3-6, the ring group represented by Ar and bound to a methine group may include at least one carbonyl group.

For example, in Chemical Formulae 1, 2, and 3-1 to 3-6, the ring group represented by Ar and bound to a methine group may include at least one carbonyl group and at least one cyano-containing moiety.

In Chemical Formulae 1, 2, and 3-1 to 3-6, the ring group represented by Ar and bound to a methine group may be represented by Chemical Formula 4.

[Chemical Formula 4]

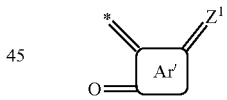

In Chemical Formula 4,

Ar' is selected from a substituted or unsubstituted 5-membered aromatic ring, a substituted or unsubstituted 6-membered aromatic ring, and a condensed ring of two or more of the foregoing rings, $Z^1$ is O or $CR^bR^c$, wherein each of $R^b$ and $R^c$ are independently selected from hydrogen, a substituted or unsubstituted $C_1$ to $C_{10}$ alkyl group, a cyano group, or a cyano-containing group, provided that at least one of $R^b$ and $R^c$ is a cyano group or a cyano-containing group.

For example, the ring group represented by Ar and bound to a methine group may be a condensed ring of a substituted or unsubstituted 5-membered aromatic ring and a substituted or unsubstituted 6-membered aromatic ring.

In Chemical Formula 1, Chemical Formula 2, and Chemical Formulae 3-1 to 3-6, the ring group represented by Ar and bound to a methine group may be a ring group represented by one of Chemical Formulae 5-1 to 5-4.

[Chemical Formula 5-1]

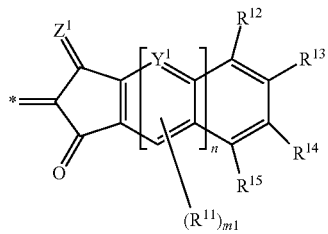

In Chemical Formula 5-1, $Z^1$ is O or $CR^bR^c$, wherein each of $R^b$ and $R^c$ are independently selected from hydrogen, a substituted or unsubstituted $C_1$ to $C_{10}$ alkyl group, a cyano group, or a cyano-containing group, provided that at least one of $R^b$ and $R^c$ is a cyano group or a cyano-containing group, $Y^1$ is selected from N and $CR^d$, wherein $R^d$ is selected from hydrogen and a substituted or unsubstituted $C_1$ to $C_{10}$ alkyl group, each of $R^{11}$, $R^{12}$, $R^{13}$, $R^{14}$, and $R^{15}$ are independently selected from hydrogen, a substituted or unsubstituted $C_1$ to $C_{30}$ alkyl group, a substituted or unsubstituted $C_6$ to $C_{30}$ aryl group, a substituted or unsubstituted C4 to $C_{30}$ heteroaryl group, a halogen, a cyano group (—CN), a cyano-containing group, and a combination thereof, or $R^{12}$ and $R^{13}$ are independently linked with each other to provide an aromatic ring and $R^{14}$ and $R^{15}$ are independently linked with each other to provide an aromatic ring, m1 is 0 or 1, and n is 0 or 1.

[Chemical Formula 5-2]

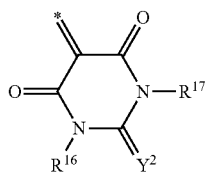

In Chemical Formula 5-2, $Y^2$ is selected from O, S, Se, Te, and $C(R^e)(CN)$ wherein $R^e$ is selected from hydrogen, a cyano group (—CN), and a $C_1$ to $C_{10}$ alkyl group, and each of $R^{16}$ and $R^{17}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted C4 to $C_{30}$ heteroaryl group, a halogen, a cyano group (—CN), and a combination thereof.

[Chemical Formula 5-3]

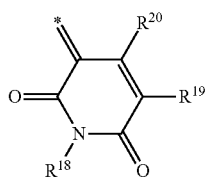

In Chemical Formula 5-3, each of $R^{18}$ to $R^{20}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted C4 to $C_{30}$ heteroaryl group, a halogen, a cyano group (—CN), a cyano-containing group, and a combination thereof.

[Chemical Formula 5-4]

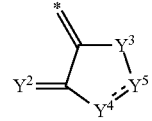

In Chemical Formula 5-4, $Y^2$ is selected from O, S, Se, Te, and $C(R^e)(CN)$ wherein $R^e$ is selected from hydrogen, a cyano group (—CN), and a $C_1$ to $C_{10}$ alkyl group, $Y^3$ is selected from O, S, Se, and Te, $Y^4$ is N or $NR^f$, $Y^5$ is selected from $CR^g$, C=O, C=S, $C=(CR^h)(CN)$, and Chemical Formula 5-4, at least one of $Y^2$ and $Y^5$ is C=O, each of $R^f$, $R^g$, and $R^h$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted C4 to $C_{30}$ heteroaryl group, a halogen, a cyano group (—CN), a cyano-containing group, and a combination thereof, and optionally $Y^4$ and $Y^5$ are linked with each other to provide a fused ring with a $Y^4$-$Y^5$-containing pentagonal ring of Chemical Formula 5-4. For example, the fused ring with the $Y^4$-$Y^5$-containing pentagonal ring may be a benzimidazole or indole ring.

The ring group represented by Chemical Formula 5-1 may be, for example a ring group represented by Chemical Formula 5-1-1, 5-1-2, or 5-1-3.

[Chemical Formula 5-1-1]

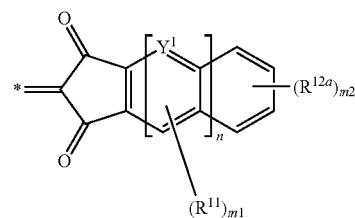

[Chemical Formula 5-1-2]

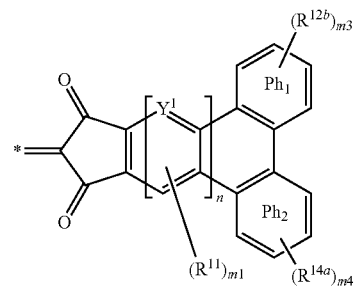

-continued

[Chemical Formula 5-1-3]

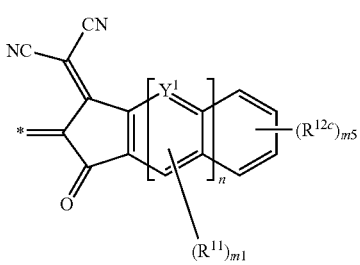

In Chemical Formulae 5-1-1, 5-1-2, and 5-1-3, $Y^1$, $R^{11}$, m1, and n are the same as in Chemical Formula 5-1, each of $R^{12a}$, $R^{12b}$, $R^{12c}$, and $R^{14a}$ are independently selected from hydrogen, a substituted or unsubstituted $C_1$ to $C_{30}$ alkyl group, a substituted or unsubstituted $C_6$ to $C_{30}$ aryl group, a substituted or unsubstituted $C_4$ to $C_{30}$ heteroaryl group, a halogen, a cyano group (—CN), a cyano-containing group, and a combination thereof, each of m2, m3, m4, and m5 are independently an integer ranging from 0 to 4, and each of Ph1 and Ph2 denote a fused phenylene ring. One of Ph1 and Ph2 may be optionally omitted.

The ring group represented by Chemical Formula 5-2 may be, for example a ring group represented by Chemical Formula 5-2-1 or 5-2-2.

[Chemical Formula 5-2-1]

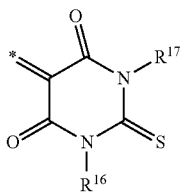

[Chemical Formula 5-2-2]

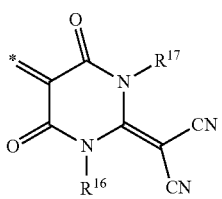

In Chemical Formulae 5-2-1 and 5-2-2, $R^{16}$ and $R^{17}$ are the same as in Chemical Formula 5-2.

The ring group represented by Chemical Formula 5-3 may be, for example a ring group represented by Chemical Formula 5-3-1 or 5-3-2.

[Chemical Formula 5-3-1]

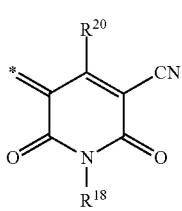

[Chemical Formula 5-3-2]

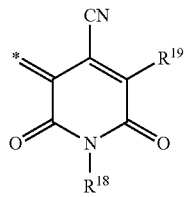

In Chemical Formulae 5-3-1 and 5-3-2, $R^{18}$ to $R^{20}$ are the same as in Chemical Formula 5-3.

The ring group represented by Chemical Formula 5-4 may be, for example a ring group represented by Chemical Formula 5-4-1, 5-4-2, 5-4-3, or 5-4-4.

[Chemical Formula 5-4-1]

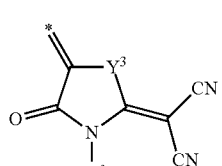

[Chemical Formula 5-4-2]

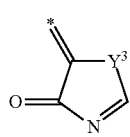

[Chemical Formula 5-4-3]

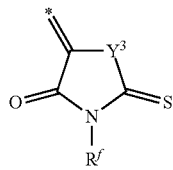

[Chemical Formula 5-4-4]

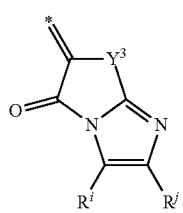

In Chemical Formulae 5-4-1, 5-4-2, 5-4-3, and 5-4-4, $Y^3$ and $R^f$ are the same as in Chemical Formula 5-4, and in Chemical Formula 5-4-4, each of $R^i$ and $R^j$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted C6 to $C_{30}$ aryl group, a substituted or unsubstituted $C_4$ to $C_{30}$ heteroaryl group, a halogen, a cyano group (—CN), a cyano-containing group, and a combination thereof, or optionally $R^i$ and $R^j$ are linked with each other to provide a fused ring. The fused ring may be a 5-membered or 6-membered aromatic ring or a hetero aromatic ring.

The compound may be a compound represented by one of Chemical Formulae 6-1 to 6-4.

[Chemical Formula 6-1]

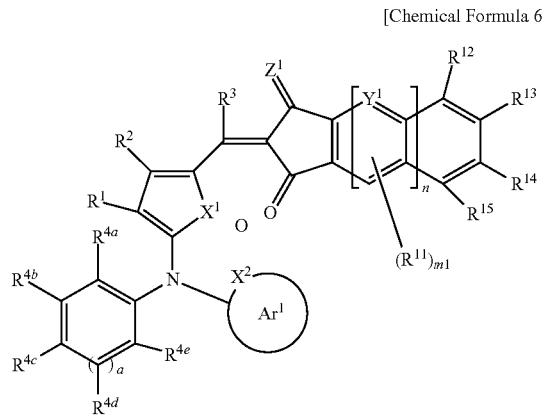

[Chemical Formula 6-2]

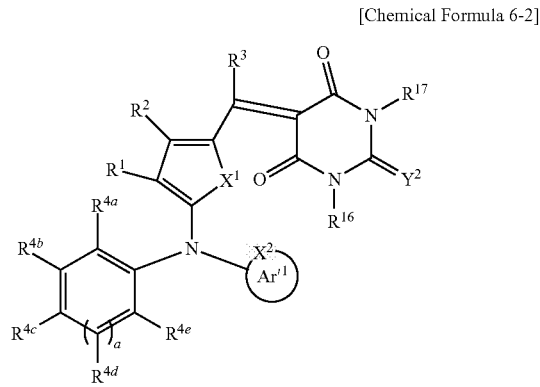

In Chemical Formula 6-1, $X^1$ is selected from Se, Te, O, $NR^a$, $S(=O)$, $S(=O)_2$, and $SiR^bR^c$, wherein $R^a$, $R^b$, and $R^c$ are selected from hydrogen and a substituted or unsubstituted $C_1$ to $C_{10}$ alkyl group, each of $R^1$ to $R^3$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted C6 to $C_{30}$ aryl group, a substituted or unsubstituted $C_3$ to $C_{30}$ heteroaryl group, a halogen, a cyano group (—CN), a cyano-containing group, and a combination thereof, $Z^1$ is O or $CR^bR^c$, wherein each of $R^b$ and $R^c$ are independently selected from hydrogen, a substituted or unsubstituted $C_1$ to $C_{10}$ alkyl group, a cyano group, or a cyano-containing group, provided that at least one of $R^b$ and $R^c$ is a cyano group or a cyano-containing group, $Y^1$ is selected from N and $CR^d$, wherein $R^d$ is selected from hydrogen and a substituted or unsubstituted $C_1$ to $C_{10}$ alkyl group, each of $R^{11}$, $R^{12}$, $R^{13}$, $R^{14}$, and $R^{15}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted C6 to $C_{30}$ aryl group, a substituted or unsubstituted $C_4$ to $C_{30}$ heteroaryl group, a halogen, a cyano group (—CN), a cyano-containing group, and a combination thereof, or $R^{12}$ and $R^{13}$ are independently linked with each other to provide an aromatic ring and $R^{14}$ and $R^{15}$ are independently linked with each other to provide an aromatic ring, m1 is 0 or 1, n is 0 or 1, each of $R^{4a}$ to $R^{4e}$ are independently selected from hydrogen, a substituted or unsubstituted $C_1$ to $C_{30}$ alkyl group, a substituted or unsubstituted C6 to $C_{30}$ aryl group, a substituted or unsubstituted $C_3$ to $C_{30}$ heteroaryl group, a halogen, a cyano group (—CN), a cyano-containing group, and a combination thereof, or optionally two adjacent groups of $R^{4a}$ to $R^{4e}$ are linked with each other to provide a 5-membered aromatic ring or a 6-membered aromatic ring, a is an integer of 0 or 1, $X^2$ is nitrogen (N), and $Ar^{r1}$ is heteroaryl group including at least one nitrogen (N) at an ortho position with respect to a bond with the nitrogen (N).

In Chemical Formula 6-2, $X^1$ is selected from Se, Te, O, $NR^a$, $S(=O)$, $S(=O)_2$, and $SiR^bR^c$, wherein each of $R^a$, $R^b$, and $R^c$ are selected from hydrogen and a substituted or unsubstituted $C_1$ to $C_{10}$ alkyl group, $Y^2$ is selected from O, S, Se, Te, and $C(R^e)(CN)$ wherein $R^e$ is selected from hydrogen, a cyano group (—CN), and a $C_1$ to $C_{10}$ alkyl group, each of $R^1$, $R^2$, $R^3$, $R^{16}$, and $R^{17}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted C6 to $C_{30}$ aryl group, a substituted or unsubstituted $C_4$ to $C_{30}$ heteroaryl group, a halogen, a cyano group (—CN), a cyano-containing group, and a combination thereof, each of $R^{4a}$ to $R^{4e}$ are independently selected from hydrogen, a substituted or unsubstituted $C_1$ to $C_{30}$ alkyl group, a substituted or unsubstituted C6 to $C_{30}$ aryl group, a substituted or unsubstituted $C_3$ to $C_{30}$ heteroaryl group, a halogen, a cyano group (—CN), a cyano-containing group, and a combination thereof, or optionally two adjacent groups of $R^{4a}$ to $R^{4e}$ are linked with each other to provide a 5-membered aromatic ring or a 6-membered aromatic ring, a is an integer of 0 or 1, $X^2$ is nitrogen (N), and $Ar^{r1}$ is heteroaryl group including at least one nitrogen (N) at an ortho position with respect to a bond with the nitrogen (N).

[Chemical Formula 6-3]

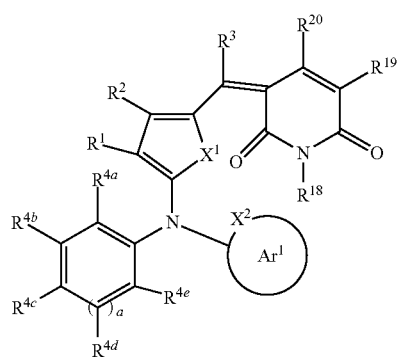

In Chemical Formula 6-3, $X^1$ is selected from Se, Te, O, $NR^a$, $S(=O)$, $S(=O)_2$, and $SiR^bR^c$, wherein $R^a$, $R^b$, and $R^c$ are selected from hydrogen and a substituted or unsubstituted $C_1$ to $C_{10}$ alkyl group, each of $R^1$, $R^2$, $R^3$, $R^{18}$, $R^{19}$, and $R^{20}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted C6 to $C_{30}$ aryl group, a substituted or unsubstituted $C_4$ to $C_{30}$ heteroaryl group, a halogen, a cyano group (—CN), a cyano-containing group, and a combination thereof, each of $R^{4a}$ to $R^{4e}$ are independently selected from hydrogen, a substituted or unsubstituted $C_1$ to $C_{30}$ alkyl group, a substituted or unsubstituted C6 to $C_{30}$ aryl group, a substituted or unsubstituted $C_3$ to $C_{30}$ heteroaryl group, a halogen, a cyano group (—CN), a cyano-containing group, and a combination thereof, or optionally two adjacent groups of $R^{4a}$ to $R^{4e}$ are linked with each other to provide a 5-membered aromatic ring or a 6-membered aromatic ring, a is an integer of 0 or 1, $X^2$ is nitrogen (N), and $Ar'^1$ is heteroaryl group including at least one nitrogen (N) at an ortho position with respect to a bond with the nitrogen (N).

[Chemical Formula 6-4]

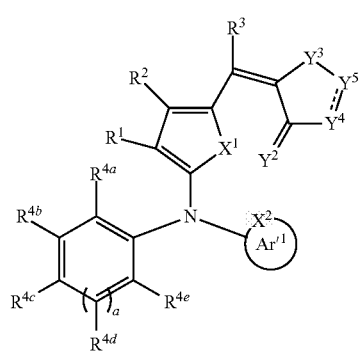

In Chemical Formula 6-4, $X^1$ is selected from Se, Te, O, $NR^a$, $S(=O)$, $S(=O)_2$, and $SiR^bR^c$, wherein each of $R^a$, $R^b$, and $R^c$ are selected from hydrogen and a substituted or unsubstituted $C_1$ to $C_{10}$ alkyl group, $Y^2$ is selected from O, S, Se, Te, and $C(R^e)(CN)$ wherein $R^e$ is selected from hydrogen, a cyano group (—CN), and a $C_1$ to $C_{10}$ alkyl group, $Y^3$ is selected from O, S, Se, and Te, $Y^4$ is N or $NR^f$, $Y^5$ is selected from $CR^g$, $C=O$, $C=S$, $C=(CR^h)(CN)$, and Chemical Formula 5-4, at least one of $Y^2$ and $Y^5$ is $C=O$, each of $R^1$, $R^2$, $R^3$, $R^f$, $R^g$, and $R^h$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_4$ to $C_{30}$ heteroaryl group, a halogen, a cyano group (—CN), a cyano-containing group, and a combination thereof, optionally $Y^4$ and $Y^5$ are linked with each other to provide a fused ring with a $Y^4$-$Y^5$-containing pentagonal ring of Chemical Formula 5-4, each of $R^{4a}$ to $R^{4e}$ are independently selected from hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, or optionally two adjacent groups of $R^{4a}$ to $R^{4e}$ are linked with each other to provide a 5-membered aromatic ring or a 6-membered aromatic ring, a is an integer of 0 or 1, $X^2$ is nitrogen (N), and $Ar'^1$ is a heteroaryl group including at least one nitrogen (N) at an ortho position with respect to a bond with the nitrogen (N).

The compound of Chemical Formula 1 may be, for example a compound represented by Chemical Formulae 7-1, 7-2, 7-3, and 7-4 but is not limited thereto.

[Chemical Formula 7-1]

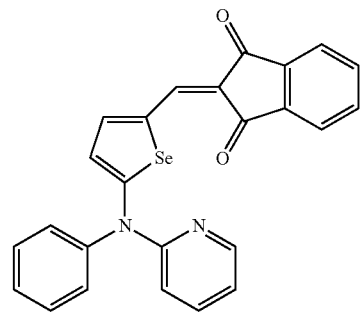

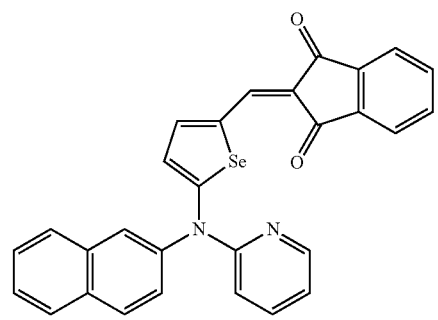

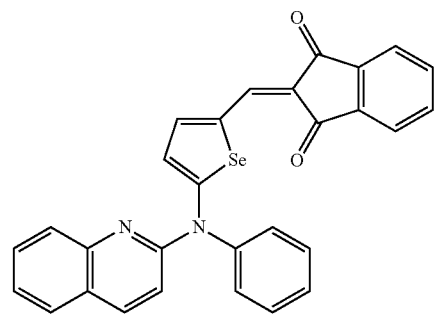

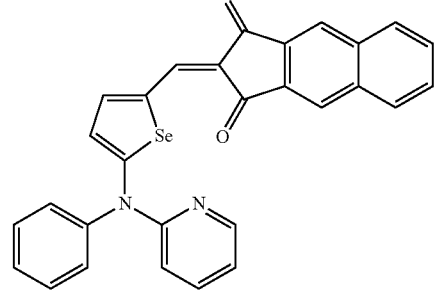

-continued
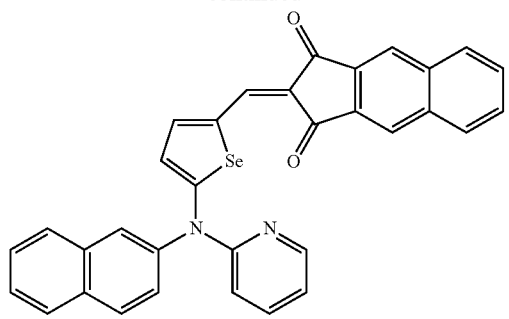
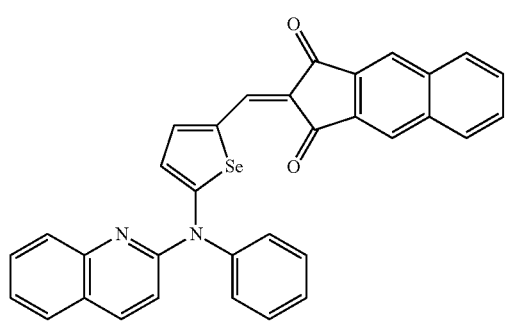
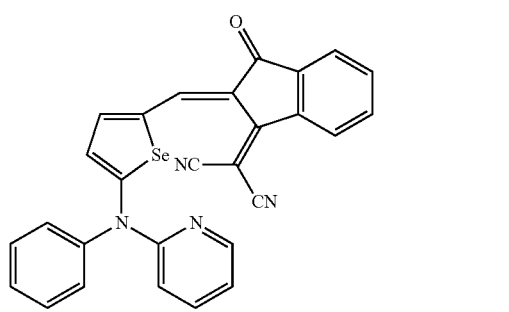
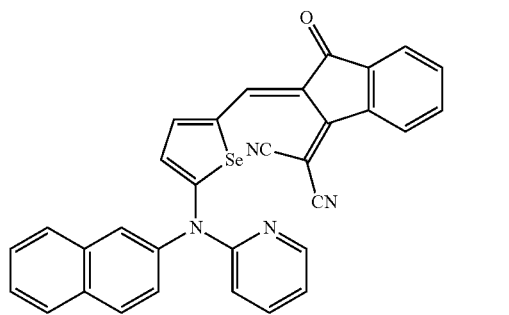
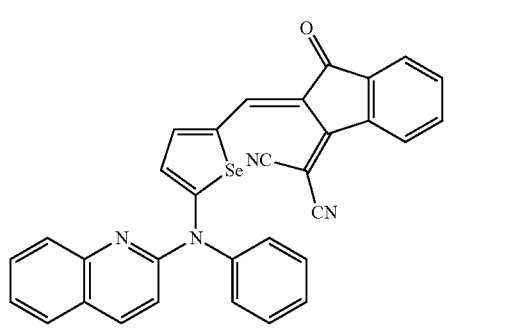
-continued
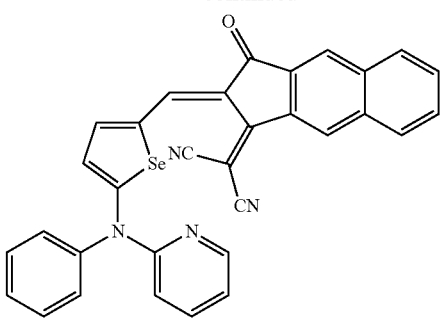
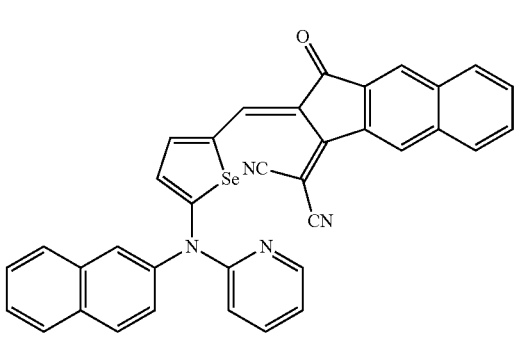
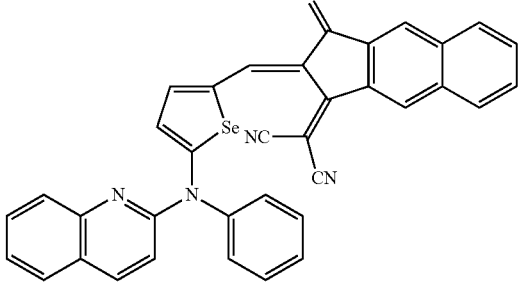
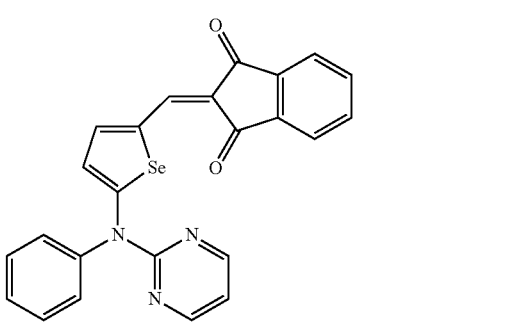
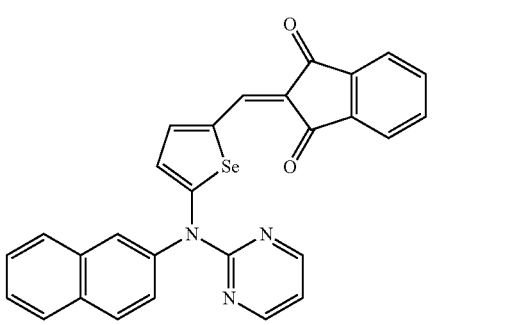

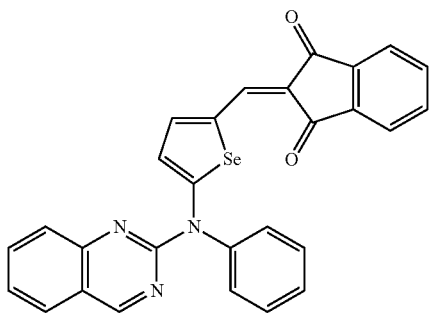
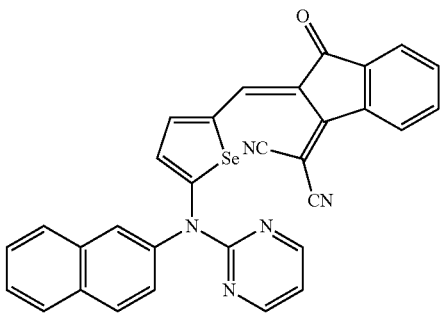
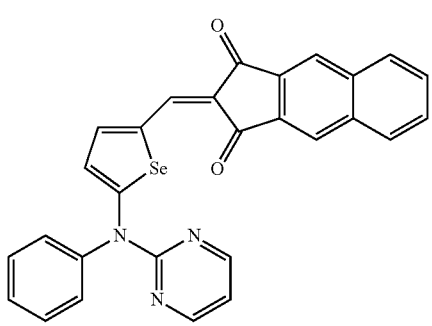
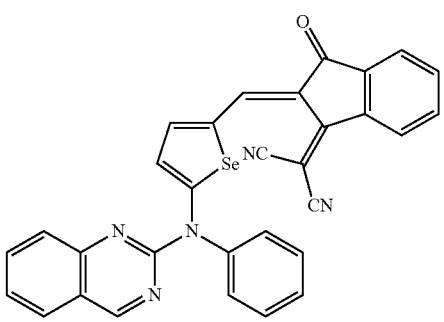
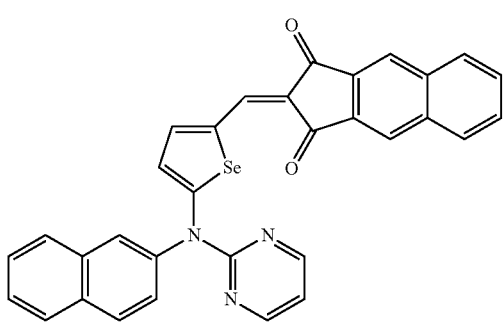
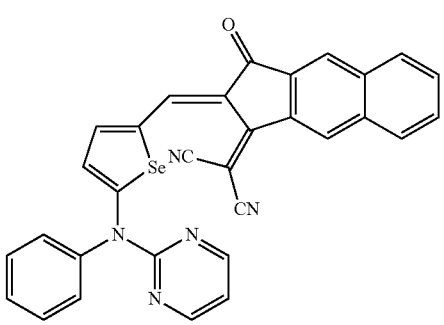
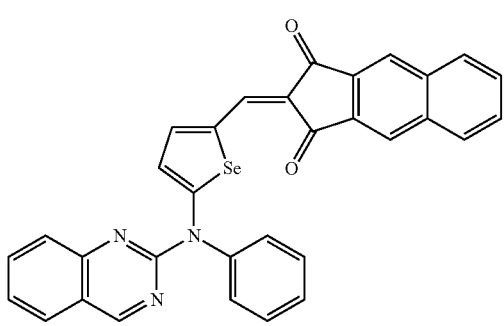
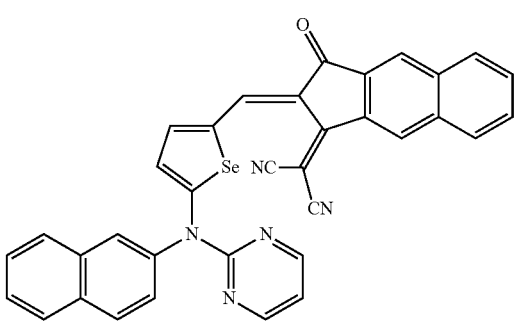
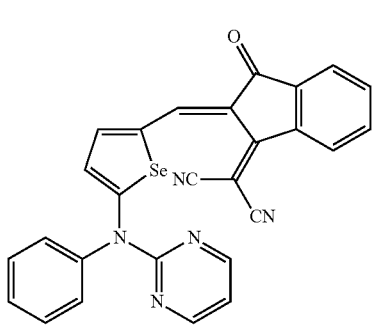
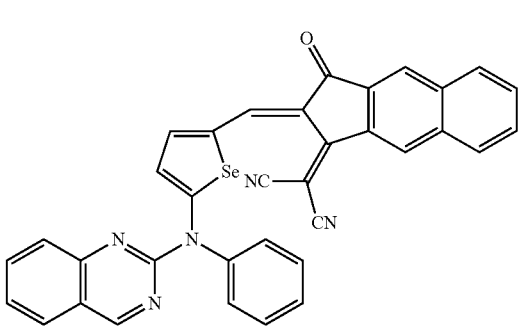

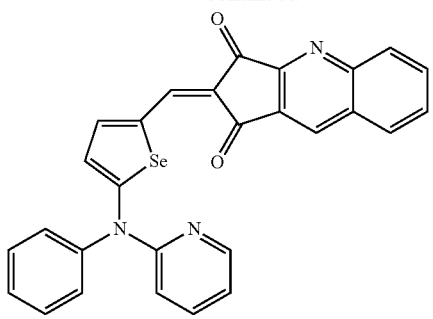
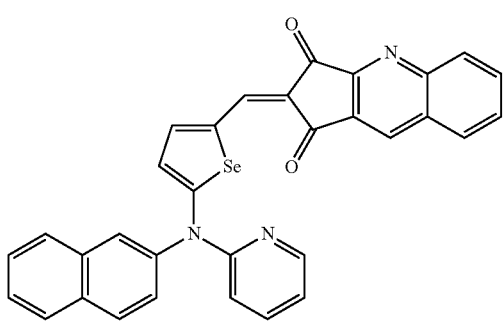
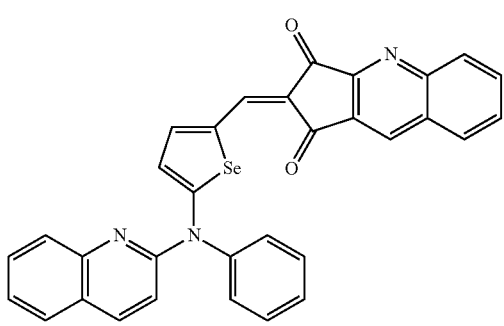
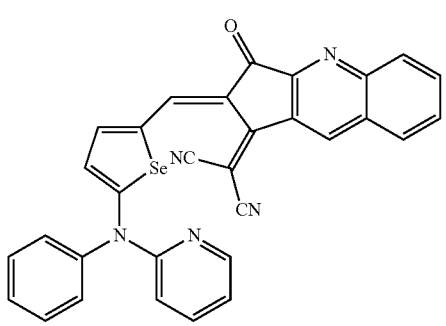
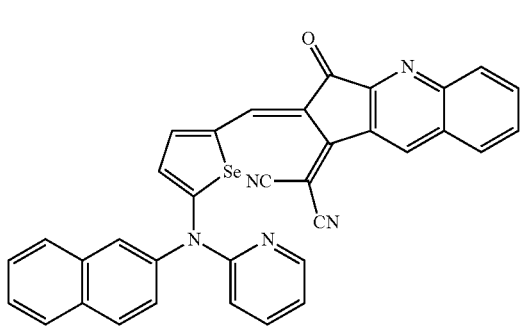
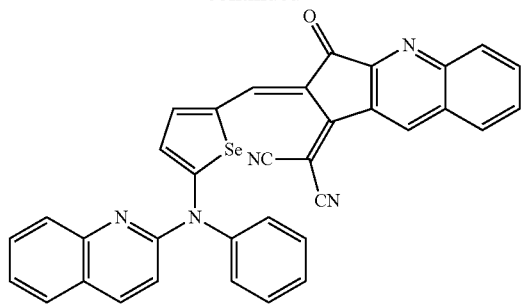
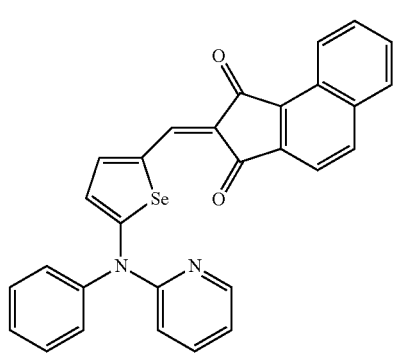
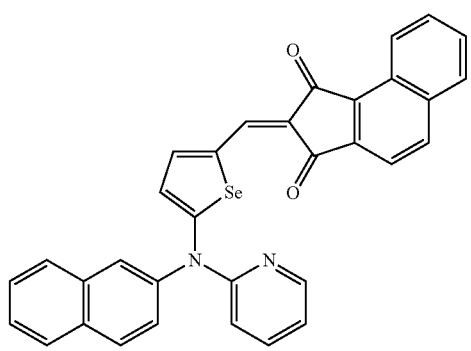
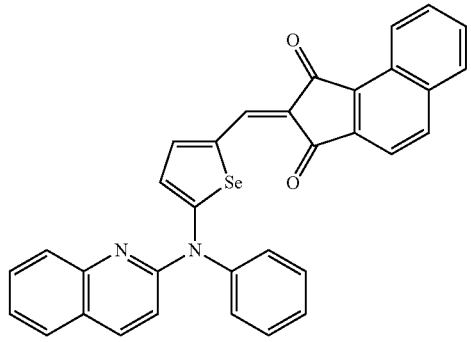
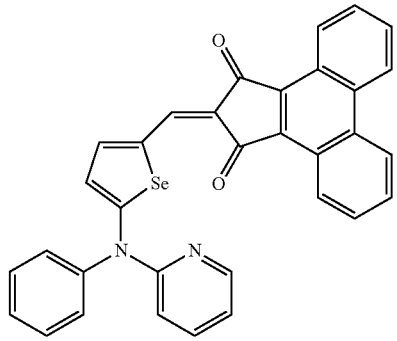

33
-continued

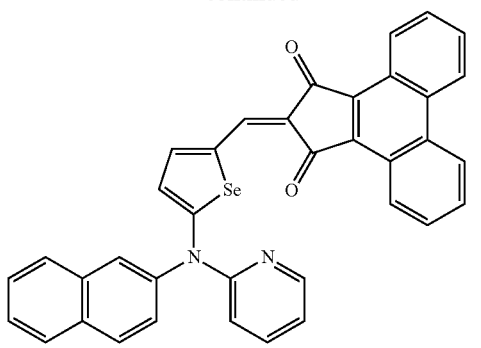

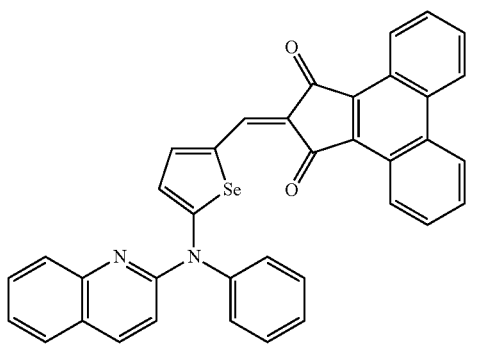

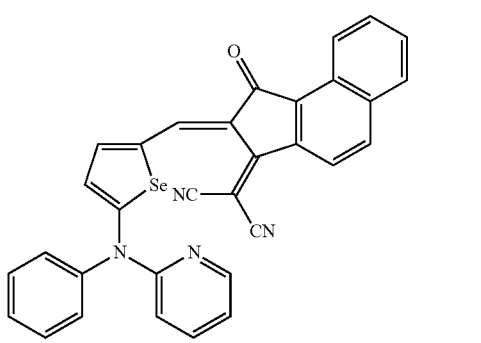

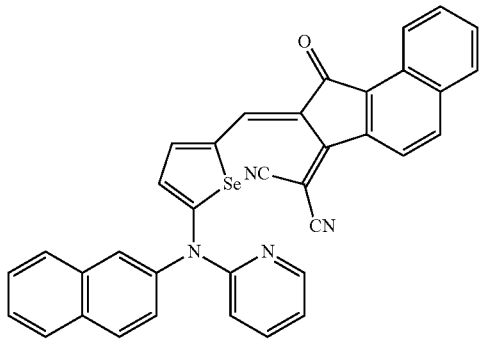

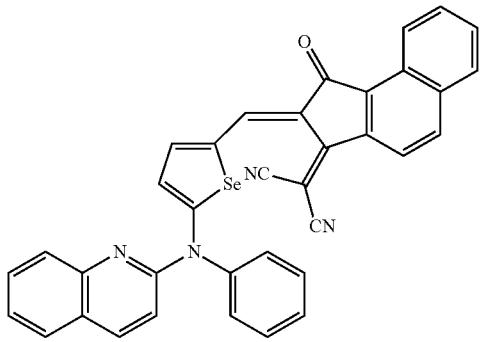

34
-continued

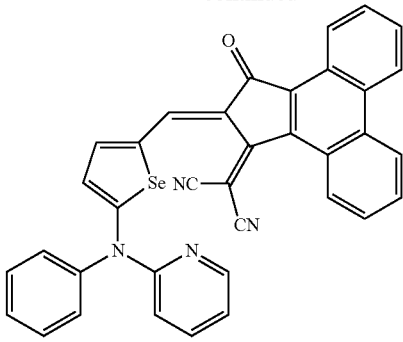

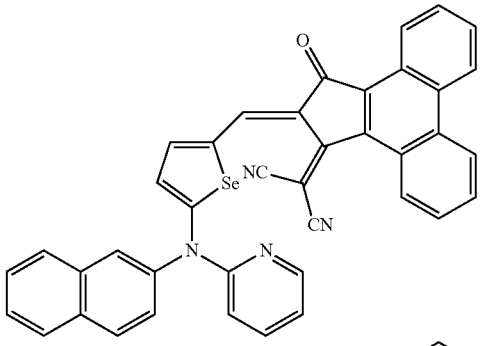

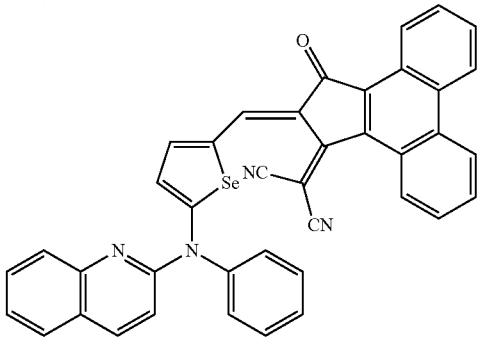

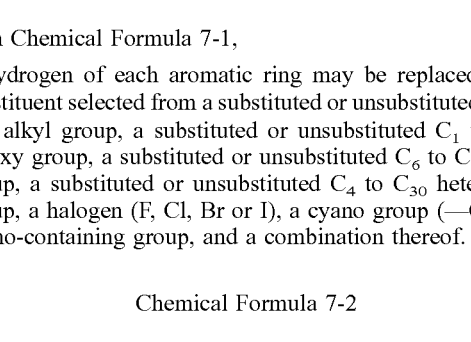

In Chemical Formula 7-1, hydrogen of each aromatic ring may be replaced by a substituent selected from a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_4$ to $C_{30}$ heteroaryl group, a halogen (F, Cl, Br or I), a cyano group (—CN), a cyano-containing group, and a combination thereof.

Chemical Formula 7-2

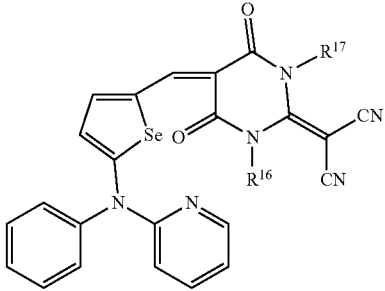

35
-continued
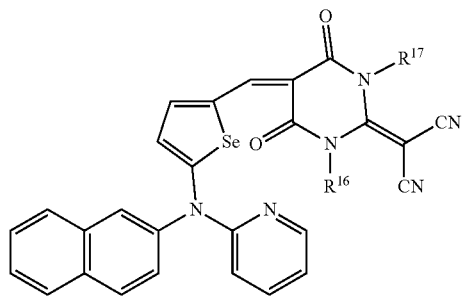
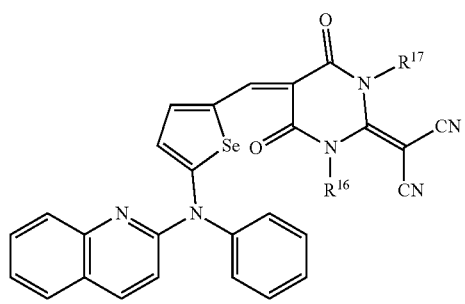
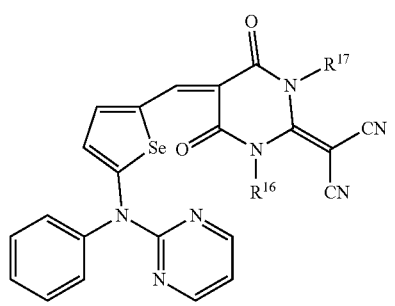
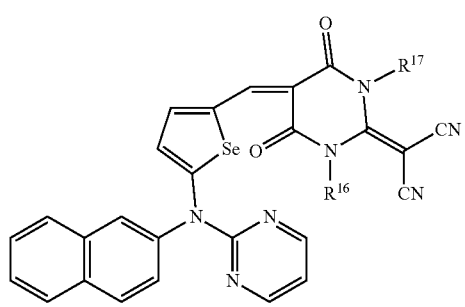
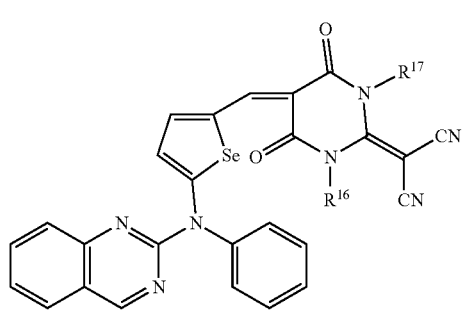
36
-continued
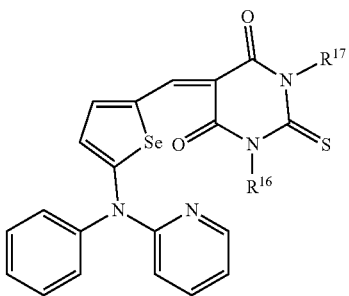
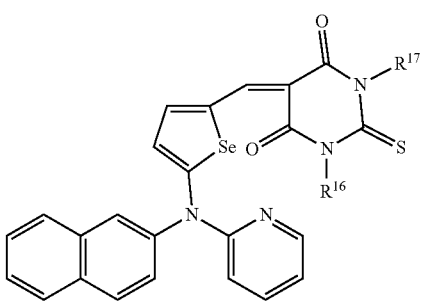
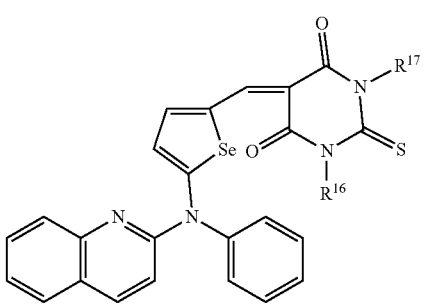
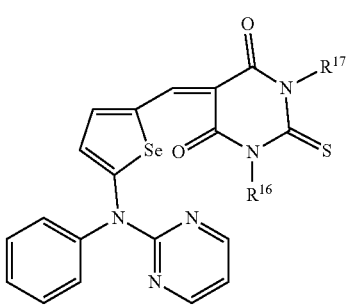
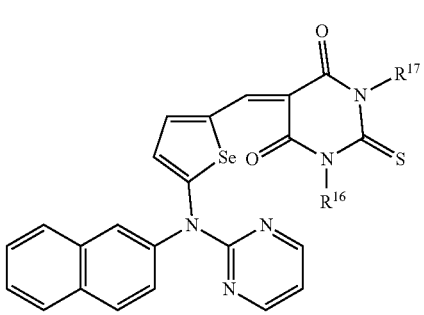

-continued

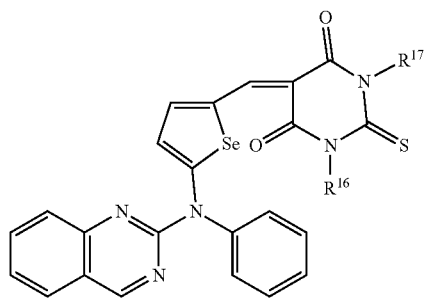

In Chemical Formula 7-2, $R^{16}$ and $R^{17}$ are the same as in Chemical Formula 5-2, and hydrogen of each aromatic ring may be replaced by a substituent selected from a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_4$ to $C_{30}$ heteroaryl group, a halogen (F, Cl, Br or I), a cyano group (—CN), a cyano-containing group, and a combination thereof.

Chemical Formula 7-3

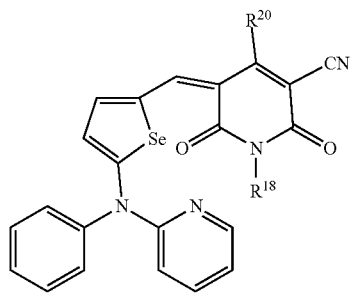

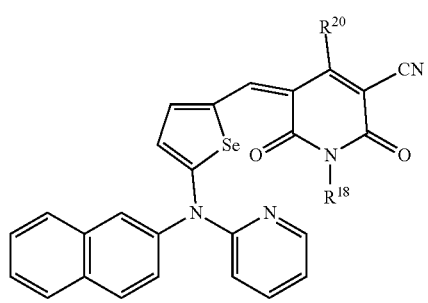

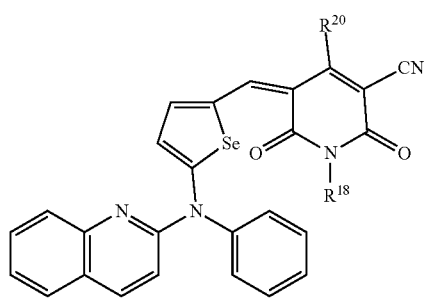

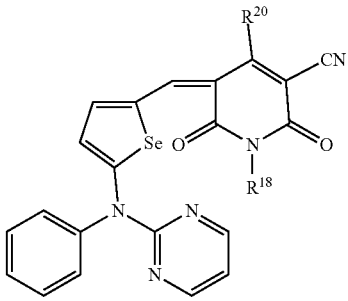

-continued

[Chemical Formula 7-4]

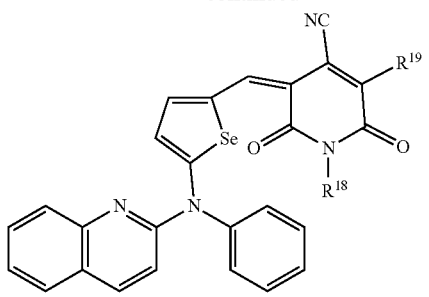
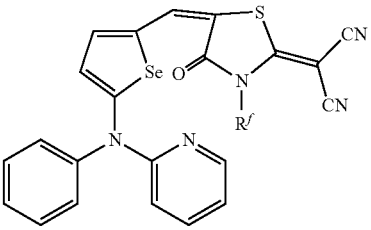

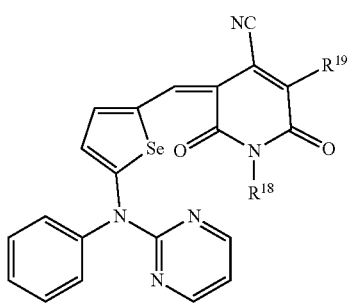
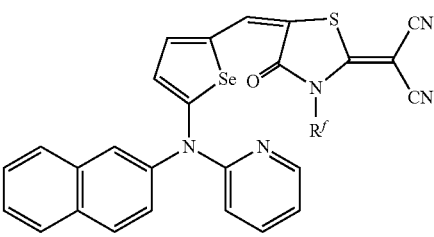

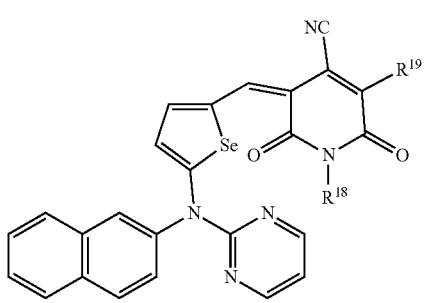
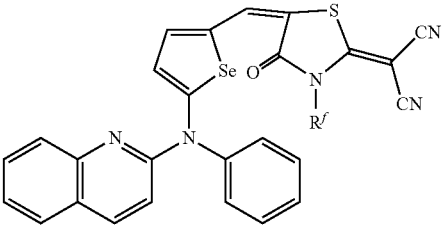

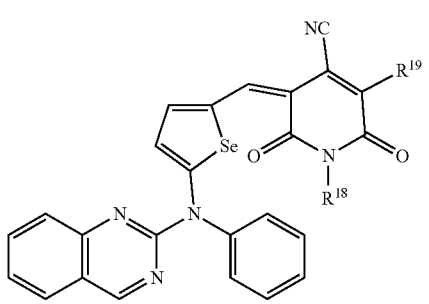
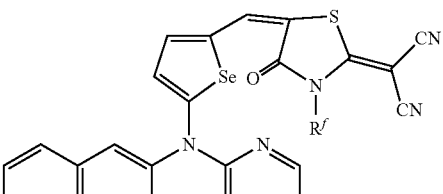

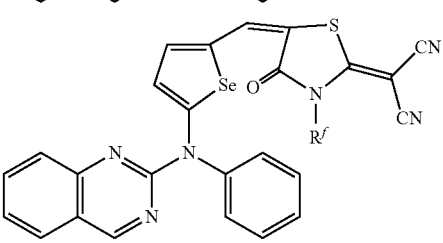

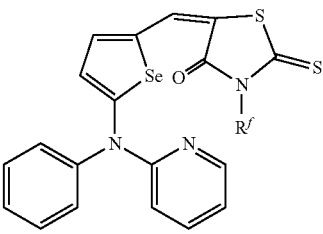

In Chemical Formula 7-3, each of $R^{18}$, $R^{19}$, and $R^{20}$ are the same as in Chemical Formula 5-3, and hydrogen of each aromatic ring may be replaced by a substituent selected from a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_4$ to $C_{30}$ heteroaryl group, a halogen (F, Cl, Br or I), a cyano group (—CN), a cyano-containing group, and a combination thereof.

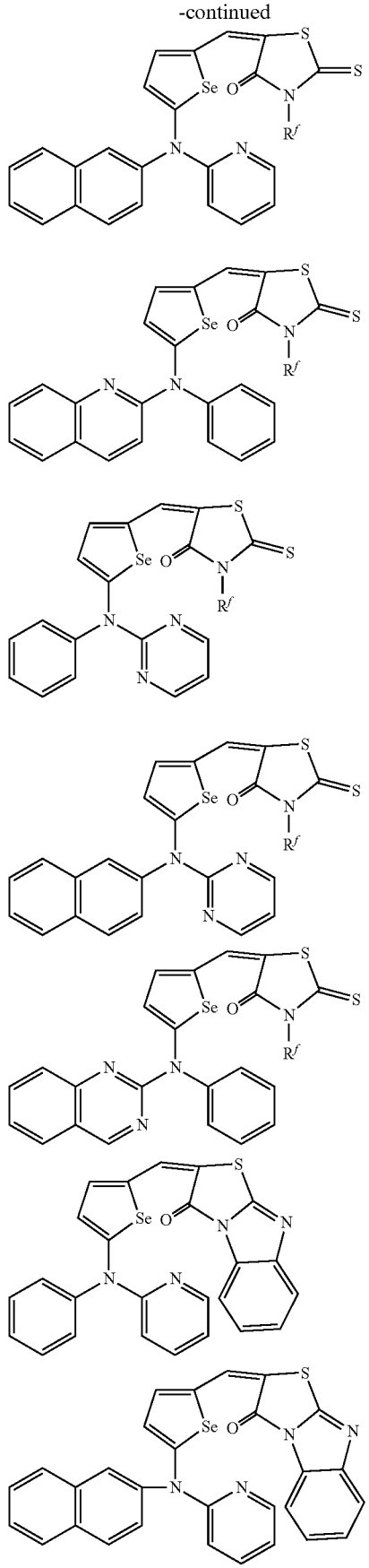

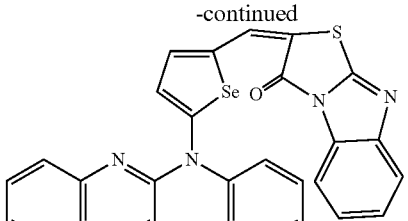

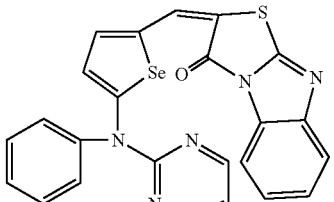

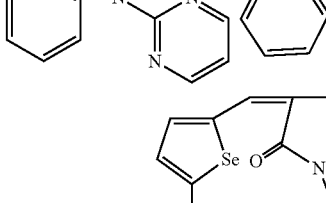

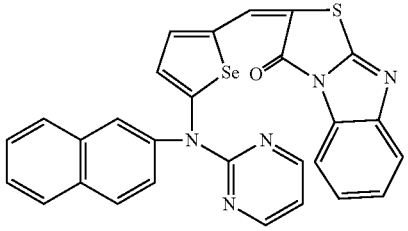

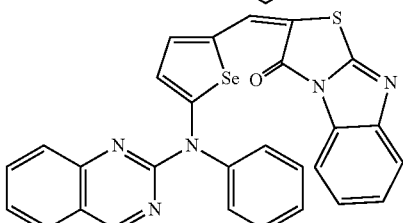

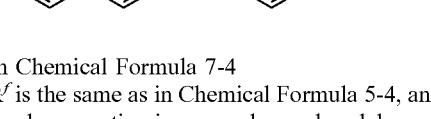

In Chemical Formula 7-4

$R^f$ is the same as in Chemical Formula 5-4, and hydrogen of each aromatic ring may be replaced by a substituent selected from a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group (e.g., phenyl group), a substituted or unsubstituted $C_4$ to $C_{30}$ heteroaryl group, a halogen (F, Cl, Br or I), a cyano group (—CN), a cyano-containing group, and a combination thereof.

The compound is a compound selectively absorbing light in a green wavelength region, and may have a maximum absorption wavelength ($\lambda_{max}$) in a wavelength region of greater than or equal to about 510 nm and less than about 560 nm, for example about 520 nm to about 555 nm, and thus may be usefully applicable to an active layer of a photoelectric device. Particularly, when it has a maximum absorption wavelength ($\lambda_{max}$) in a wavelength region of about 520 nm to about 555 nm, an image sensor including the photoelectric device has reduced color difference ($\Delta E^*ab$).

The compound may exhibit a light absorption curve having a full width at half maximum (FWHM) of about 50 nm to about 110 nm, in a thin film state. Herein, the FWHM is a width of a wavelength corresponding to half of a maximum absorption point. As used herein, when specific definition is not otherwise provided, it may be defined by absorbance measured by UV-Vis spectroscopy. When the full width at half maximum (FWHM) is within the range, selectivity in a green wavelength region may be increased. The thin film may be a thin film deposited under a vacuum condition.

The compound may be formed into a thin film using a deposition method. The deposition method may provide a uniform thin film and have small inclusion possibility of impurities into the thin film, but when the compound has a lower melting point than a temperature for the deposition, a product decomposed from the compound may be deposited and thus performance of a device may be deteriorated. Accordingly, the compound desirably has a higher melting point than the deposition temperature. The compound has, for example, greater than or equal to about 10° C. higher melting point than the deposition temperature and thus may be desirably used for the deposition.

Because the compound works as a p-type semiconductor, the compound may be appropriately used, as long as it has a higher LUMO level than an n-type semiconductor. For example, when the compound is mixed with an n-type material such as fullerene, the compound desirably has a higher LUMO level than 4.2 eV than the fullerene having a LUMO level of 4.2 eV. As for the appropriate HOMO-LUMO level of the compound, when the compound has a HOMO level ranging from about 5.0 eV to about 5.8 eV and an energy bandgap ranging from about 1.9 eV to about 2.3 eV, the LUMO level of the compound is in a range of about 3.9 eV to about 2.7 eV. The compound having a HOMO level, an LUMO level, and an energy bandgap within the ranges may be used as a p-type semiconductor compound effectively absorbing light in a green wavelength region, and thus has high external quantum efficiency (EQE) and resultantly improves photoelectric conversion efficiency.

In example embodiments, in view of a thin film formation, a stably depositable compound is desirable and thus the compound has a molecular weight of about 300 to about 1500. However, even though the compound has a molecular weight out of the range, a depositable compound may be used without limitation. In addition, when the compound is formed to form a thin film using a coating process, a compound that is dissolved in a solvent and coated may be used without limitation.

The compound may be used as a p-type semiconductor compound.

Hereinafter, an organic photoelectric device including the compound according to an example embodiment is described with reference to drawings.

FIG. 1 is a cross-sectional view showing an organic photoelectric device according to example embodiments.

Referring to FIG. 1, an organic photoelectric device 100 according to example embodiments includes a first electrode 10 and a second electrode 20, and an active layer 30 between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may at least partially comprise, for example, a transparent conductor including indium tin oxide (ITO) or indium zinc oxide (IZO), or a metal thin layer of a thin single layer or multilayer. When one of the first electrode 10 and the second electrode 20 is a non-light-transmitting electrode, the first electrode 10 and/or the second electrode 20 may at least partially comprise, for example, an opaque conductor including aluminum (Al).

The active layer 30 includes a p-type semiconductor and an n-type semiconductor to form a pn junction, and absorbs external light to generate excitons and then separates the generated excitons into holes and electrons.

The active layer 30 includes the compound represented by Chemical Formula 1. The compound may act as a p-type semiconductor compound in the active layer 30.

The compound is a compound selectively absorbing light in a green wavelength region, and the active layer 30 including the compound may have a maximum absorption wavelength (λmax) in a wavelength region of greater than or equal to about 510 nm and less than about 560 nm, for example about 520 nm to about 555 nm.

The active layer 30 may exhibit a light absorption curve having a relatively narrow full width at half maximum (FWHM) of about 50 nm to about 110 nm, for example about 50 nm to about 100 nm. Accordingly, the active layer 30 has high selectivity for light in a green wavelength region.

The active layer may have an absorption coefficient of greater than or equal to about $5.5 \times 10^4$ cm$^{-1}$, for example about $5.8 \times 10^4$ cm$^{-1}$ to about $10 \times 10^4$ cm$^{-1}$ or about $7.0 \times 10^4$ cm$^{-1}$ to about $10 \times 10^4$ cm$^{-1}$ when including the compound Chemical Formula 1 and C60 in a volume ratio of about 0.9:1 to about 1.1:1, for example about 1:1.

The active layer 30 may further include an n-type semiconductor compound for forming a pn junction.

The n-type semiconductor compound may be sub-phthalocyanine or a sub-phthalocyanine derivative, fullerene or a fullerene derivative, thiophene or a thiophene derivative, or a combination thereof.

The fullerene may include C60, C70, C76, C78, C80, C82, C84, C90, C96, C240, C540, a mixture thereof, a fullerene nanotube, etc. The fullerene derivative may refer to compounds of these fullerenes having a substituent attached thereto. The fullerene derivative may include a substituent such as alkyl group, aryl group, or a heterocyclic group. Examples of the aryl groups and heterocyclic groups may be are a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a benzimidazole ring, an imidazopyridine ring, a quinolizidine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, an xanthene ring, a phenoxathin ring, a phenothiazine ring, or a phenazine ring.

The sub-phthalocyanine or the sub-phthalocyanine derivative may be represented by Chemical Formula 8.

[Chemical Formula 8]

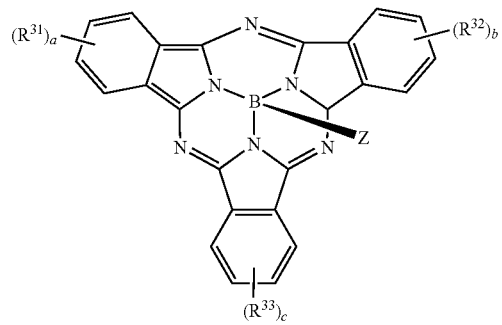

In Chemical Formula 8, each of $R^{31}$ to $R^{33}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted C6 to $C_{30}$ aryl group, a substituted or unsubstituted $C_3$ to $C_{30}$ heteroaryl group, a halogen, a halogen-containing group, and a combination thereof, each of a, b, and c are integers ranging from 1 to 3, and Z is a monovalent substituent.

For example, Z may be a halogen or a halogen-containing group, for example, F, Cl, a F-containing group, or a Cl-containing group.

The halogen refers to F, Cl, Br, or I and the halogen-containing group refers to alkyl group where at least one of hydrogen is replaced by F, Cl, Br, or I.

The thiophene derivative may be, for example represented by Chemical Formula 9 or 10 but is not limited thereto.

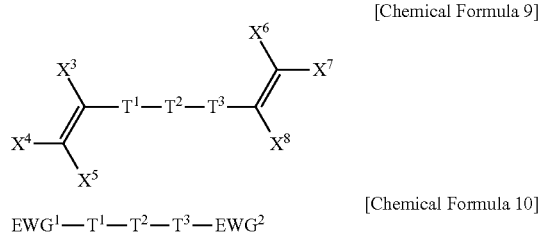

[Chemical Formula 9]

EWG$^1$—T$^1$—T$^2$—T$^3$—EWG$^2$     [Chemical Formula 10]

In Chemical Formulae 9 and 10, each of $T^1$, $T^2$, and $T^3$ are aromatic rings including substituted or unsubstituted thiophene moieties, each of $T^1$, $T^2$, and $T^3$ are independently present or are fused to each other, each of $X^3$ to $X^8$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_3$ to $C_{30}$ heterocyclic group, a cyano group, or a combination thereof, and each of EWG$^1$ and EWG$^2$ are independently electron withdrawing groups.

For example, in Chemical Formula 9, at least one of $X^3$ to $X^8$ is an electron withdrawing group, for example a cyano-containing group.

The active layer 30 may further include a second p-type semiconductor compound selectively absorbing green light. The p-type semiconductor compound may be a compound represented by Chemical Formula 11.

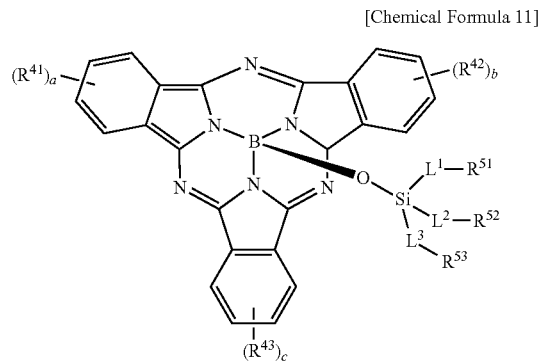

[Chemical Formula 11]

In Chemical Formula 11, each of $R^{41}$ to $R^{43}$ are independently selected from hydrogen, a substituted or unsubstituted $C_1$ to $C_{30}$ aliphatic hydrocarbon group, a substituted or unsubstituted $C_6$ to $C_{30}$ aromatic hydrocarbon group, a substituted or unsubstituted $C_1$ to $C_{30}$ aliphatic heterocyclic group, a substituted or unsubstituted C2 to $C_{30}$ aromatic heterocyclic group, a substituted or unsubstituted $C_1$ to $C_{30}$ alkoxy group, a substituted or unsubstituted $C_6$ to $C_{30}$ aryloxy group, thiol group, a substituted or unsubstituted $C_6$ to $C_{30}$ alkylthio group, a substituted or unsubstituted $C_6$ to $C_{30}$ arylthio group, a cyano group, a cyano-containing group, a halogen, a halogen-containing group, a substituted or unsubstituted sulfonyl group (e.g., a substituted or unsubstituted $C_1$ to $C_{30}$ aminosulfonyl group, a substituted or unsubstituted $C_1$ to $C_{30}$ alkylsulfonyl group or a substituted or unsubstituted $C_6$ to $C_{30}$ arylsulfonyl group), or a combination thereof, or two adjacent groups of $R^{41}$ to $R^{43}$ are linked with each other to provide a fused ring, each of $L^1$ to $L^3$ are independently a single bond, a substituted or unsubstituted $C_1$ to $C_{30}$ alkylene group, a substituted or unsubstituted $C_6$ to $C_{30}$ arylene group, a divalent substituted or unsubstituted $C_3$ to $C_{30}$ heterocyclic group, or a combination thereof, each of $R^{51}$ to $R^{53}$ are independently a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_3$ to $C_{30}$ heterocyclic group, a substituted or unsubstituted $C_1$ to $C_{30}$ alkoxy group, a substituted or unsubstituted amine group (e.g., a substituted or unsubstituted $C_1$ to $C_{30}$ alkylamine group or a substituted or unsubstituted $C_6$ to $C_{30}$ arylamine group), a substituted or unsubstituted silyl group, or a combination thereof, and each of a to c are independently an integer ranging from 0 to 4.

The second p-type semiconductor compound selectively absorbing green light may be included in an amount of about 500 to about 1500 parts by weight based on 100 parts by weight of the compound represented by Chemical Formula 1.

The active layer 30 may be a single layer or a multilayer. The active layer 30 may be, for example, an intrinsic layer (I layer), a p-type layer/I layer, an I layer/n-type layer, a p-type layer/I layer/n-type layer, a p-type layer/n-type layer, etc.

The intrinsic layer (I layer) may include the compound of Chemical Formula 1 and the n-type semiconductor compound in a ratio of about 1:100 to about 100:1. The compound of Chemical Formula 1 and the n-type semiconductor compound may be included in a ratio ranging from about 1:50 to about 50:1 within the range, for example, about 1:10 to about 10:1, for example, about 1:1. When the compound of Chemical Formula 1 and the n-type semiconductor compound have a composition ratio within the range, an exciton may be effectively produced, and a pn junction may be effectively formed.

The p-type layer may include the semiconductor compound of Chemical Formula 1, and the n-type layer may include the n-type semiconductor compound.

The active layer 30 may have a thickness of about 1 nm to about 500 nm and specifically, about 5 nm to about 300 nm. When the active layer 30 has a thickness within the range, the active layer may effectively absorb light, effectively separate holes from electrons, and deliver them, thereby effectively improving photoelectric conversion efficiency. An optimal thickness of a thin film may be, for example, determined by an absorption coefficient of the active layer 30, and may be, for example, a thickness being capable of absorbing light of at least about 70% or more, for example about 80% or more, and for another example about 90%.

In the organic photoelectric device 100, when light enters from the first electrode 10 and/or second electrode 20, and when the active layer 30 absorbs light in a given or predetermined wavelength region, excitons may be produced from the inside. The excitons are separated into holes and electrons in the active layer 30, and the separated holes are transported to an anode that is one of the first electrode 10 and the second electrode 20 and the separated electrons are transported to the cathode that is the other of and the first electrode 10 and the second electrode 20 so as to flow a current in the organic photoelectric device.

Hereinafter, an organic photoelectric device according to another example embodiment is described with reference to FIG. 2.

Figure 2:
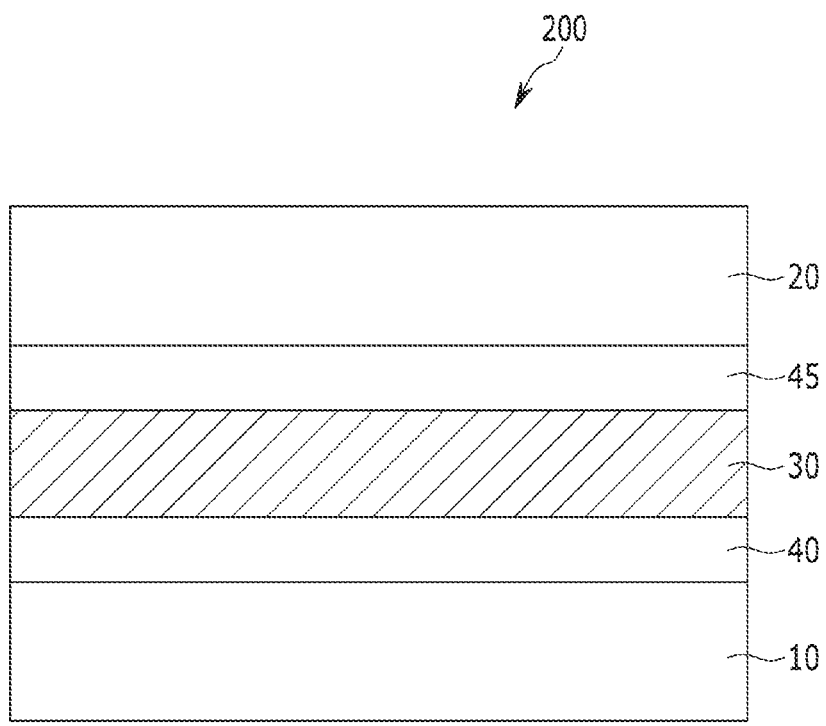
FIG. 2 is a cross-sectional view showing an organic photoelectric device according to example embodiments.

FIG. 2 is a cross-sectional view showing an organic photoelectric device according to example embodiments.

Referring to FIG. 2, an organic photoelectric device 200 according to example embodiments includes a first electrode 10 and a second electrode 20 facing each other, and an active layer 30 between the first electrode 10 and the second electrode 20, like the above example embodiment illustrated in FIG. 1.

However, the organic photoelectric device 200 according to example embodiments further includes charge auxiliary layers 40 and 45 between the first electrode 10 and the active layer 30, and the second electrode 20 and the active layer 30, unlike the above example embodiment illustrated in FIG. 1. The charge auxiliary layers 40 and 45 may facilitate the transfer of holes and electrons separated from the active layer 30, so as to increase efficiency.

The charge auxiliary layers 40 and 45 may be at least one selected from a hole injection layer (HIL) for facilitating hole injection, a hole transport layer (HTL) for facilitating hole transport, an electron blocking layer (EBL) for reducing or preventing electron transport, an electron injection layer (EIL) for facilitating electron injection, an electron transport layer (ETL) for facilitating electron transport, and a hole blocking layer (HBL) for reducing or preventing hole transport.

The charge auxiliary layers 40 and 45 may include, for example, an organic material, an inorganic material, or an organic/inorganic material. The organic material may be an organic compound having hole or electron characteristics, and the inorganic material may be, for example, a metal oxide such as molybdenum oxide, tungsten oxide, nickel oxide, etc.

The hole transport layer (HTL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

Either one of the charge auxiliary layers 40 and 45 may be omitted.

The organic photoelectric device may be applied to various fields, for example a solar cell, an image sensor, a photo-detector, a photo-sensor, and an organic light emitting diode (OLED), but is not limited thereto.

Hereinafter, an example of an image sensor including the organic photoelectric device is described referring to drawings. As an example of an image sensor, an organic CMOS image sensor is described.

Figure 3:
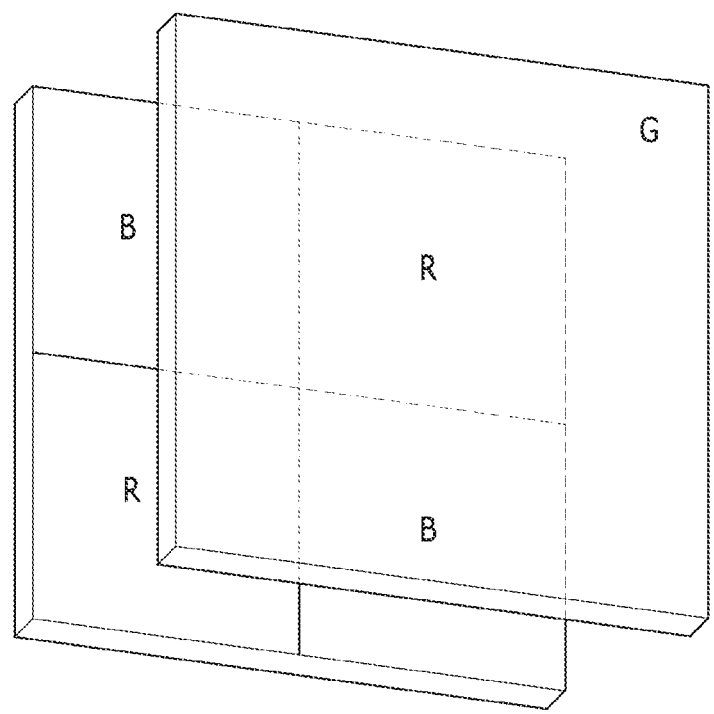
FIG. 3 is a schematic top plan view showing an organic CMOS image sensor according to example embodiments.
Figure 4:
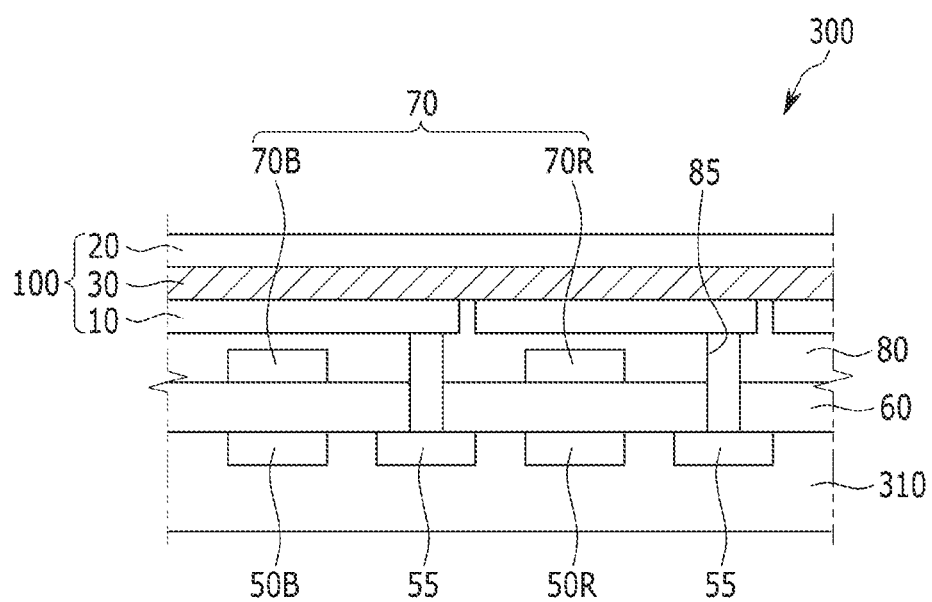
FIG. 4 is a cross-sectional view showing the organic CMOS image sensor of FIG. 3.

FIG. 3 is a schematic top plan view showing an organic CMOS image sensor according to example embodiments, and FIG. 4 is a cross-sectional view showing the organic CMOS image sensor of FIG. 3.

Referring to FIGS. 3 and 4, an organic CMOS image sensor 300 according to example embodiments includes a semiconductor substrate 310 integrated with photo-sensing devices 50B and 50R, a transmission transistor (not shown), a charge storage 55, a lower insulation layer 60, a color filter layer 70, an upper insulation layer 80, and an organic photoelectric device 100.

The semiconductor substrate 310 may be a silicon substrate, and is integrated with the photo-sensing device 50, the transmission transistor (not shown), and the charge storage 55. The photo-sensing devices 50R and 50B may be photodiodes.

The photo-sensing devices 50B and 50R, the transmission transistor (not shown), and/or the charge storage 55 may be integrated in each pixel, and as shown in the drawing, the photo-sensing devices 50B and 50R may be respectively included in a blue pixel and a red pixel and the charge storage 55 may be included in a green pixel.

The photo-sensing devices 50B and 50R sense light, the information sensed by the photo-sensing devices may be transferred by the transmission transistor, the charge storage 55 is electrically connected to the organic photoelectric device 100, and the information of the charge storage 55 may be transferred by the transmission transistor.

In the drawings, the photo-sensing devices 50B and 50R are, for example, arranged in parallel without limitation, and the blue photo-sensing device 50B and the red photo-sensing device 50R may be stacked in a vertical direction.

A metal wire (not shown) and a pad (not shown) are formed on the semiconductor substrate 110. In order to decrease signal delay, the metal wire and pad may at least partially comprise a metal having relatively low resistivity, for example, aluminum (Al), copper (Cu), silver (Ag), and alloys thereof, but are not limited thereto. In some example embodiments, the metal wire and pad may be positioned under the photo-sensing devices 50B and 50R.

The lower insulation layer 60 is formed on the metal wire and the pad. The lower insulation layer 60 may at least partially comprise an inorganic insulating material including a silicon oxide and/or a silicon nitride, or a low dielectric constant (low K) material including SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70B formed in the blue pixel and selectively transmitting blue light and a red filter 70R formed in the red pixel and selectively transmitting red light. In example embodiments, a green filter is not included, but a green filter may be further included.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may not be equipped.

The upper insulation layer 80 is formed on the color filter layer 70. The upper insulation layer 80 may eliminate a step caused by the color filter layer 70 and smoothes the surface. The upper insulation layer 80 and the lower insulation layer 60 may include a contact hole (not shown) exposing a pad, and a through-hole 85 exposing the charge storage 55 of the green pixel.

The organic photoelectric device 100 is formed on the upper insulation layer 80. The organic photoelectric device 100 includes the first electrode 10, the active layer 30, and the second electrode 20 as described above.

The first electrode 10 and the second electrode 20 may be transparent electrodes, and the active layer 30 is the same as described above. The active layer 30 may selectively absorb and/or sense light in a green wavelength region and may replace a color filter of a green pixel.

When light enters from the second electrode 20, the light in a green wavelength region may be mainly absorbed in the active layer 30 and photoelectrically converted, while the light in the rest of the wavelength regions passes through first electrode 10 and may be sensed in the photo-sensing devices 50B and 50R.

As described above, the organic photoelectric devices selectively absorbing light in a green wavelength region are stacked and thereby a size of an image sensor may be decreased and a down-sized image sensor may be realized.

As described above, the compound represented by the Chemical Formula 1 may be used as a semiconductor compound, aggregation between compounds in a thin film state is inhibited, and thereby light absorption characteristics depending on a wavelength may be maintained. Thereby, green wavelength selectivity may be maintained, crosstalk caused by unnecessary absorption of other light except a green wavelength region may be decreased and sensitivity may be increased.

Figure 5:
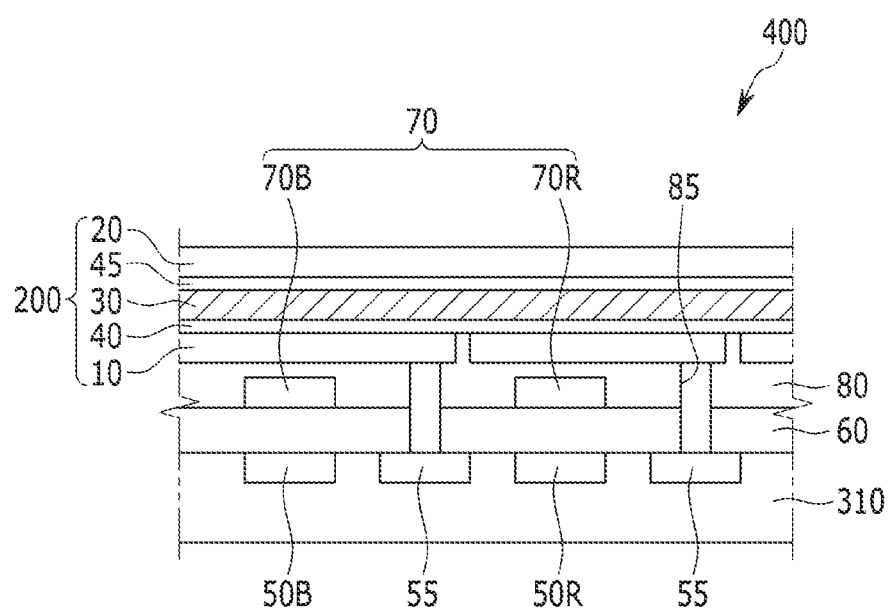
FIG. 5 is a schematic cross-sectional view showing an organic CMOS image sensor according to example embodiments.

In FIG. 4, the organic photoelectric device 100 of FIG. 1 is included, but it is not limited thereto, and thus the organic photoelectric device 200 of FIG. 2 may be applied in the same manner. FIG. 5 shows a structure of an image sensor having such a structure, and is a cross-sectional view of an organic CMOS image sensor 400 including the organic photoelectric device 200 in FIG. 2.

Figure 6:
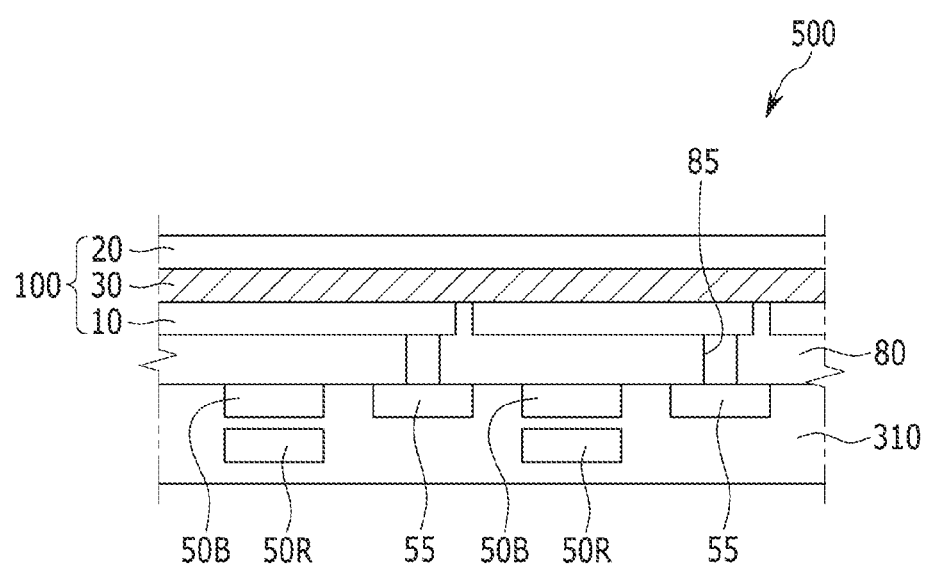
FIG. 6 is a schematic cross-sectional view showing an organic CMOS image sensor according to example embodiments.

FIG. 6 is a cross-sectional view showing the organic CMOS image sensor according to example embodiments.

Referring to FIG. 6, the organic CMOS image sensor 500 includes a semiconductor substrate 310 integrated with photo-sensing devices 50B and 50R, a transmission transistor (not shown), a charge storage 55, an insulation layer 80, and an organic photoelectric device 100, like the example embodiment illustrated in FIG. 5.

However, the organic CMOS image sensor 500 according to the example embodiment illustrated in FIG. 6 includes the blue photo-sensing device 50B and the red photo-sensing device 50R that are stacked and does not include a color filter layer 70, unlike the example embodiment illustrated in FIG. 5. The blue photo-sensing device 50B and the red photo-sensing device 50R are electrically connected to the charge storage 55, and the information of the charge storage 55 may be transferred by the transmission transistor (not shown). The blue photo-sensing device 50B and the red photo-sensing device 50R may selectively absorb light in each wavelength region depending on a stack depth.

As described above, the organic photoelectric devices selectively absorbing light in a green wavelength region are stacked and the red photo-sensing device and the blue photo-sensing device are stacked, and thereby a size of an image sensor may be decreased and a down-sized image sensor may be realized. As described above, the organic photoelectric device 100 has improved green wavelength selectivity, and crosstalk caused by unnecessary absorption light in a wavelength region except green may be decreased while increasing sensitivity.

In FIG. 6, the organic photoelectric device 100 of FIG. 1 is included, but it is not limited thereto, and thus the organic photoelectric device 200 of FIG. 2 may be applied in the same manner.

Figure 7:
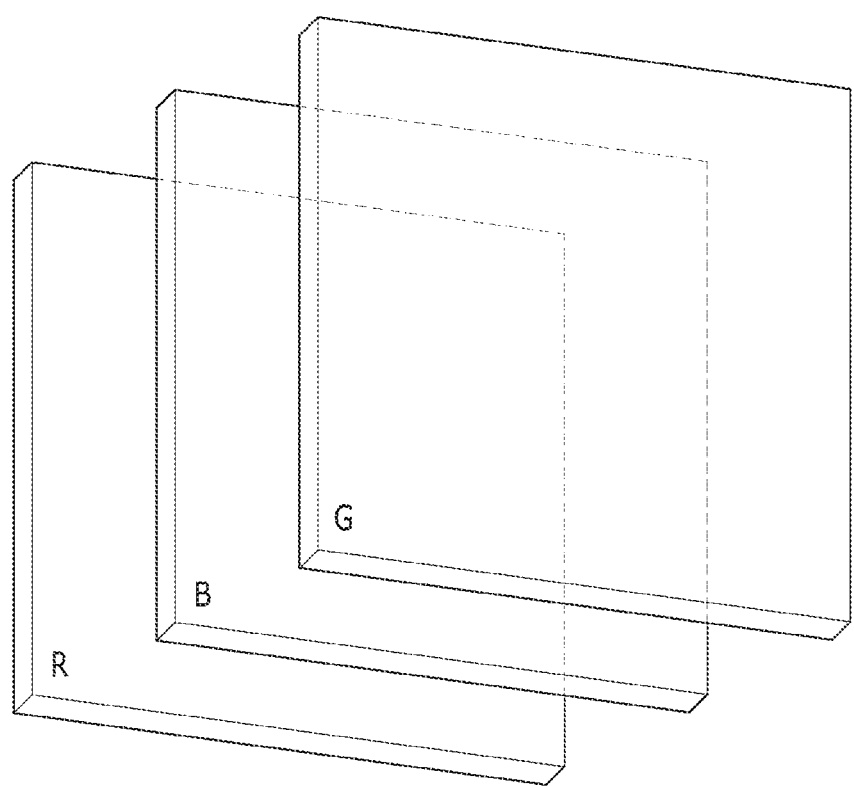
FIG. 7 is a schematic view showing an organic CMOS image sensor according to example embodiments.

FIG. 7 is a schematic view showing an organic CMOS image sensor according to example embodiments.

Referring to FIG. 7, the organic CMOS image sensor according to example embodiments includes a green photoelectric device (G) selectively absorbing light in a green wavelength region, a blue photoelectric device (B) selectively absorbing light in a blue wavelength region, and a red photoelectric device selectively absorbing light in a red wavelength region that are stacked.

In the drawing, the red photoelectric device, the green photoelectric device, and the blue photoelectric device are sequentially stacked, but the stack order may be changed without limitation.

The green photoelectric device may be the above organic photoelectric device 100, the blue photoelectric device may include electrodes facing each other and an active layer interposed therebetween and including an organic material selectively absorbing light in a blue wavelength region, and the red photoelectric device may include electrodes facing each other and an active layer interposed therebetween and including an organic material selectively absorbing light in a red wavelength region.

As described above, the organic photoelectric device selectively absorbing light in a green wavelength region, the organic photoelectric device selectively absorbing light in a red wavelength region, and the organic photoelectric device selectively absorbing light in a blue wavelength region are stacked, and thereby a size of an image sensor may be decreased and a down-sized image sensor may be realized.

The image sensor may have a color difference ($\Delta E^*ab$) of less than about 4.0, for example less than or equal to about 3.9, less than or equal to about 3.2, and less than or equal to about 1.6. The $\Delta E^*ab$ is defined as a distance between two points on a L*a*b* color space by CIE (Commission International de L'Eclairage) in 1976. For example, the color difference may be calculated according to Equation 1.

$$\Delta E = \sqrt{(\Delta L^*)^2 + (\Delta a^*)^2 + (\Delta b^*)^2} \quad \text{[Equation 1]}$$

In the Equation 1,

ΔL* denotes a change of a color coordinate L* compared with the color coordinate L* at room temperature (about 20° C. to about 25° C.), Δa* denotes a change of a color coordinate a* compared with the color coordinate a* at room temperature, and Δb* denotes a change of a color coordinate b* compared with the color coordinate b* at room temperature.

The image sensor may realize high sensitivity (YSNR10) of less than or equal to about 100 lux at a color difference (ΔE*ab) of about 3.0.

The image sensor may be applied to various electronic devices, for example, a mobile phone, a digital camera, and the like but is not limited thereto.

Hereinafter, the present disclosure is illustrated in more detail with reference to examples. However, these are examples, and the present disclosure is not limited thereto.

Synthesis Example 1: Synthesis of Compound Represented by Chemical Formula 1-1

[Chemical Formula 1-1]

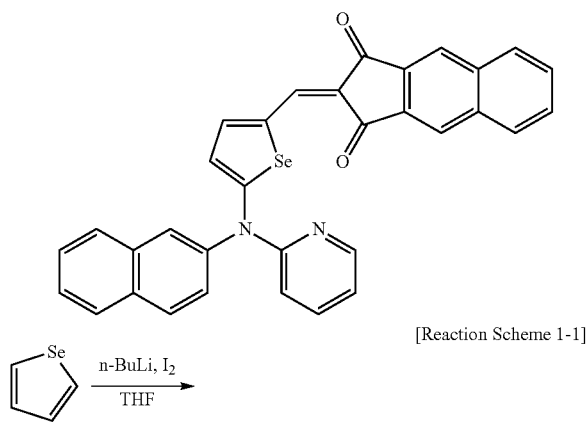

[Reaction Scheme 1-1]

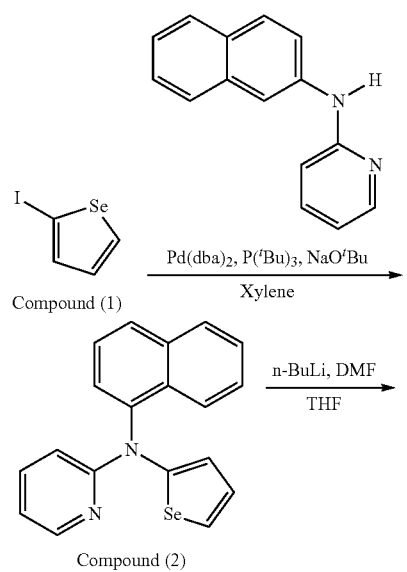

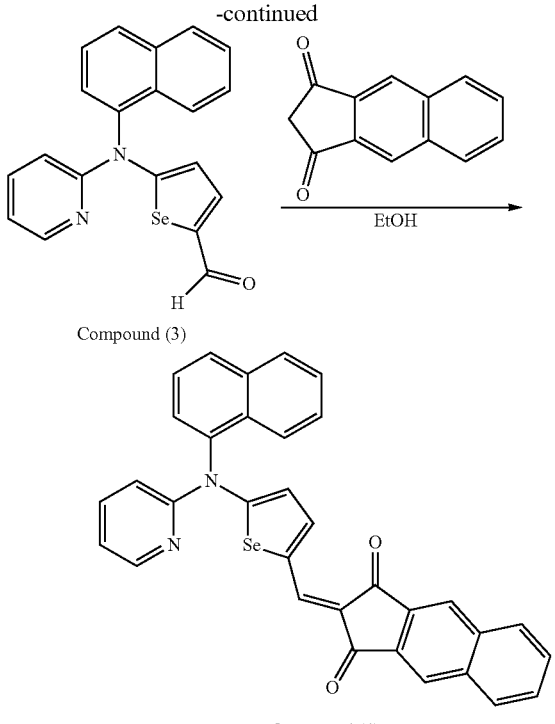

Compound (1) is synthesized in a method describe in a non-patent reference (Heterocycles 1996, 43, 1927-1935).

3.6 g (14.2 mmmol) of Compound (1), 2.8 g (12.8 mmmol) of 2-(naphthyl amino)pyridine, 10 mol % of Pd(dba)₂ (bis(dibenzylideneacetone)palladium (0)), 10 mol % of P(ᵗBu)₃ (tri-tert-butylphosphine), and 1.5 g of NaOᵗBu (sodium-t-butoxide) are heated and refluxed in 100 ml of anhydrous toluene for 5 hours. The resultant is cooled down to room temperature of 24° C. and concentrated, and a crude product obtained therefrom is purified through silica gel column chromatography to obtain 2.7 g of Compound (2) (a yield of 65%).

2.0 g (5.7 mmol) of Compound (2) is dissolved in 30 ml of anhydrous tetrahydrofuran (THF), the solution is cooled down to 0° C., and 3.9 ml of an n-BuLi solution (1.6 M of a concentration) is added thereto in a dropwise fashion within a range of 5° C. After the addition, the mixture is heated up to 40° C. and then, stirred for 30 minutes. Subsequently, the resultant is cooled down to −78° C., and 1.0 ml of anhydrous DMF is added thereto. The mixture is added to room temperature of 24° C., an ammonium chloride aqueous solution is added thereto, and the mixture is quenched and then, treated with ethyl acetate for an extraction. An organic layer therefrom is evaporated and removed to obtain a crude product. The crude product is purified through silica gel chromatography to obtain 1.0 g of Compound (3) (a yield of 47%).

0.5 g (1.3 mmol) of Compound (3) is suspended in 10 ml of ethanol, 0.3 g of 1H-cyclopenta[b]naphthalene-1,3(2H)-dione is added thereto, and the mixture is heated at 50° C. for 2 hours. The resultant is cooled down to room temperature (24° C.) and then, suction-filtered and dried to obtain 0.67 g of a crude product (a yield of 92%). The crude product is sublimation-purified to obtain 0.54 g of Compound (4) represented by Chemical Formula 1-1 (a yield of 74%, purity of 99%).

¹H NMR (300 MHz, DMSO-d₆): δ 8.8 (d, 1H), 8.5 (s, 1H), 8.4 (s, 1H), 8.2-8.3 (m, 4H), 8.2 (d, 1H), 8.1 (s, 1H), 7.9-7.6 (m, 6H), 7.5 (t, 1H), 7.4 (d, 1H), 7.3 (dd, 1H), 6.3 (d, 1H), 6.0 (d, 1H), 5.7 (s, 1H).

Synthesis Example 2: Synthesis of Compound Represented by Chemical Formula 1-2

[Chemical Formula 1-2]

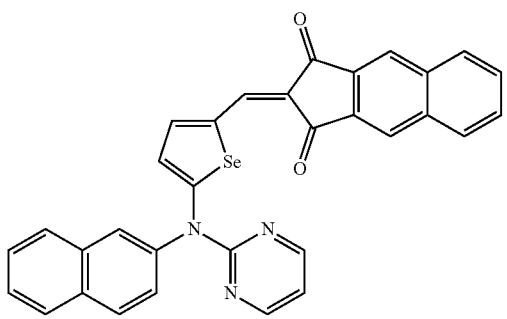

A compound represented by Chemical Formula 1-2 is synthesized according to the same method as Synthesis Example 1 except for using 2-(phenylamino)pyrimidine instead of the 2-(naphthyl amino)pyridine (a yield of 74%, purity of 99%).

¹H NMR (300 MHz, CDCl₃): δ 8.7 (s, 2H), 8.4 (d, 2H), 8.0-8.2 (m, 5H), 7.4-7.9 (m, 8H), 7.2 (dd, 1H), 6.1 (d, 1H).

Synthesis Example 3: Synthesis of Compound Represented by Chemical Formula 1-3

[Chemical Formula 1-3]

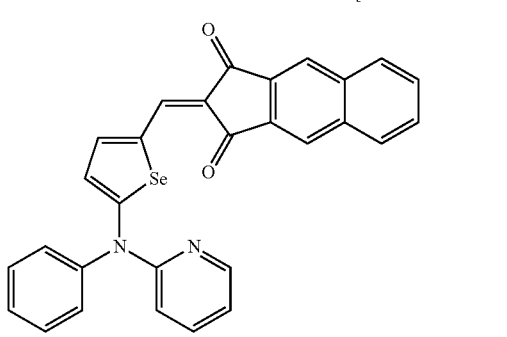

A compound represented by Chemical Formula 1-3 is synthesized according to the same method as Synthesis Example 1 except for using 2-(phenylamino)pyridine instead of the 2-(naphthyl amino)pyridine (a yield of 74%, purity of 99%).

¹H NMR (300 MHz, DMSO-d₆): δ 8.8 (d, 1H), 8.5 (s, 1H), 8.4 (s, 1H), 8.3 (m, 3H), 8.1 (s, 1H), 7.6-7.8 (m, 6H), 7.6 (d, 2H), 7.3 (dd, 1H), 6.5 (d, 1H), 6.1 (d, 1H).

Synthesis Example 4: Synthesis of Compound Represented by Chemical Formula 1-4

[Chemical Formula 1-4]

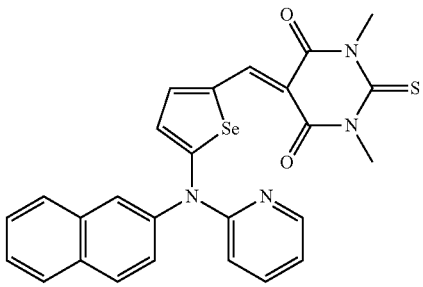

A compound represented by Chemical Formula 1-4 is synthesized according to the same method as Synthesis Example 1 except for using 1,3-dimethyl-2-thioxohexahydropyrimidine-4,6-dione instead of the 1H-cyclopenta[b]naphthalene-1,3(2H)-dione (a yield of 74%, purity of 99%).

¹H NMR (300 MHz, CDCl₃): δ 8.8 (d, 1H), 8.7 (s, 1H), 8.2 (d, 1H), 8.0 (d, 2H), 7.9 (d, 2H), 7.8 (t, 1H), 7.6 (m, 2H), 7.5 (m, 3H), 7.1 (t, 1H), 6.3 (d, 1H), 6.2 (d, 1H), 3.9 (d, 6H).

Synthesis Example 5: Synthesis of Compound Represented by Chemical Formula 1-5

[Chemical Formula 1-5]

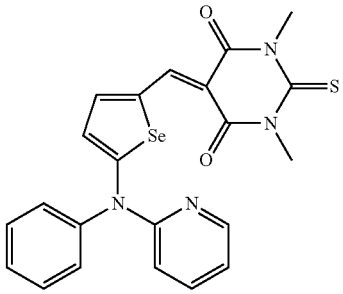

A compound represented by Chemical Formula 1-5 is synthesized according to the same method as Synthesis Example 1 except for using 2-(phenylamino)pyridine instead of the 2-(naphthylamino)pyridine and 1,3-dimethyl-2-thioxohexahydropyrimidine-4,6-dione instead of the 1H-cyclopenta[b]naphthalene-1,3(2H)-dione (a yield of 74%, purity of 99%).

¹H NMR (300 MHz, CDCl₃): δ 8.8 (d, 1H), 8.7 (s, 1H), 8.0 (d, 1H), 7.7 (m, 4H), 7.4 (d, 2H), 7.1 (t, 1H), 6.5 (d, 1H), 6.3 (d, 1H), 3.9 (d, 6H).

Comparative Synthesis Example 1: Synthesis of Compound Represented by Chemical Formula 1-6

[Chemical Formula 1-6]

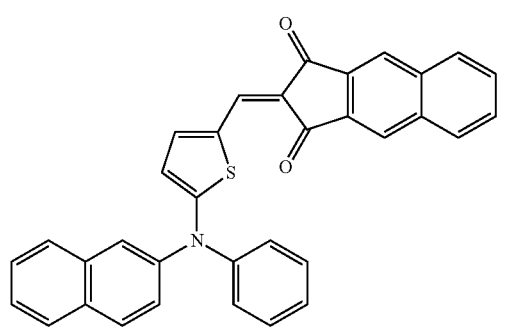

A compound represented by Chemical Formula 1-6 is synthesized according to the same method as Synthesis Example 1 except for using 2-iodothiophene instead of the compound 1 and N-(2-naphthyl)aniline instead of the 2-(naphthylamino)pyridine (a yield of 74%, purity of 99%).

$^1$H NMR (300 MHz, DMSO-d$_6$): δ 8.5 (s, 1H), 8.4 (s, 1H), 8.2-8.3 (m, 4H), 8.2 (d, 1H), 8.1 (s, 1H), 7.9-7.6 (m, 7H), 7.5 (t, 1H), 7.4 (d, 1H), 7.3 (dd, 1H), 6.3 (d, 1H), 6.0 (d, 1H), 5.7 (s, 1H).

Reference Synthesis Example 1: Synthesis of Compound Represented by Chemical Formula 1-7

[Chemical Formula 1-7]

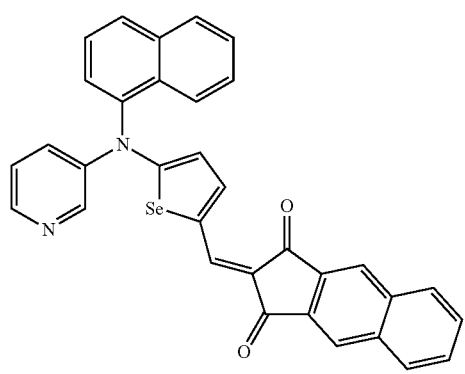

A compound represented by Chemical Formula 1-7 is synthesized according to the same method as Synthesis Example 1 except for using N-(2-naphthyl)aniline instead of the 2-(naphthyl amino)pyridine (a yield of 74%, purity of 99%).

$^1$H NMR (300 MHz, DMSO-d$_6$): δ 8.8 (s, 1H), 8.7 (d, 1H), 8.5 (s, 1H), 8.4 (s, 1H), 8.2-8.3 (m, 4H), 8.2 (d, 1H), 8.1 (s, 1H), 7.9-7.6 (m, 5H), 7.5 (t, 1H), 7.4 (d, 1H), 7.3 (dd, 1H), 6.3 (d, 1H), 6.0 (d, 1H), 5.7 (s, 1H).

Reference Synthesis Example 2: Synthesis of Compound Represented by Chemical Formula 1-8

[Chemical Formula 1-8]

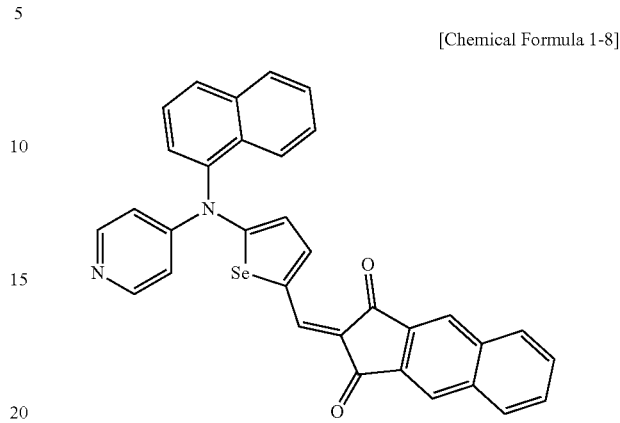

A compound represented by Chemical Formula 1-7 is synthesized according to the same method as Synthesis Example 1 except for using 4-(naphthylamino)pyridine instead of the 2-(naphthyl amino)pyridine (a yield of 74%, purity of 99%).

$^1$H NMR (300 MHz, DMSO-d$_6$): δ 8.8 (d, 2H), 8.5 (s, 1H), 8.4 (s, 1H), 8.2-8.3 (m, 4H), 8.2 (d, 1H), 8.1 (s, 1H), 7.9-7.6 (m, 5H), 7.5 (t, 1H), 7.4 (d, 1H), 7.3 (dd, 1H), 6.3 (d, 1H), 6.0 (d, 1H), 5.7 (s, 1H).

Light Absorption Characteristics of Compound of Synthesis Examples 1 to 5, Comparative Synthesis Example 1, and Reference Synthesis Examples 1 and 2

Light absorption characteristics (absorption wavelength, absorption intensity, and a full width at half maximum (FWHM)) of the compounds of Synthesis Examples 1 to 5, Comparative Synthesis Example 1, and Reference Synthesis Examples 1 and 2 depending on a wavelength are evaluated. The light absorption characteristics are evaluated in a solution state and a thin film state.

The light absorption characteristics in the solution state are evaluated by dissolving 5 mg of each compound of Synthesis Examples 1 to 5, Comparative Synthesis Example 1, and Reference Synthesis Examples 1 and 2 in 250 ml of toluene and ten times diluting each solution.

The light absorption characteristics in the thin film state are evaluated by thermally depositing each compound of Synthesis Examples 1 to 5, Comparative Synthesis Example 1, and Reference Synthesis Examples 1 and 2 and C60 in a volume ratio of 1:1 under a high vacuum (<10$^{-7}$ Torr) at a speed of 0.5 to 1.0 Å/s to respectively form a 70 nm-thick thin film and radiating an ultraviolet (UV)-visible ray (UV-Vis) thereto with Cary 5000 UV spectroscopy (Varian Medical System, Inc.). The light absorption characteristics results of the compounds of Synthesis Examples 1 to 5, Comparative Synthesis Example 1, and Reference Synthesis Examples 1 and 2 are shown in Table 1.

TABLE 1

| | Solution | | | Thin film | | |
|---|---|---|---|---|---|---|
| | λmax (nm) | absorption coefficient ($10^5$ cm$^{-1}$) | FWHM (nm) | λmax (nm) | absorption coefficient ($10^4$ cm$^{-1}$) | FWHM (nm) |
| Synthesis Example 1 | 533 | 1.2 | 40 | 552 | 7.8 | 105 |
| Synthesis Example 2 | 526 | 1.2 | 34 | 540 | 7.9 | 100 |
| Synthesis Example 3 | 537 | 1.1 | 32 | 554 | 8.2 | 108 |
| Synthesis Example 4 | 515 | 1.2 | 27 | 530 | 7.4 | 97 |
| Synthesis Example 5 | 515 | 1.2 | 28 | 520 | 9.1 | 95 |
| Comparative Synthesis Example 1 | 540 | 1.0 | 51 | 560 | 5.3 | 110 |
| Reference Synthesis Example 1 | 540 | 0.9 | 52 | 560 | 5.3 | 111 |
| Reference Synthesis Example 2 | 541 | 0.9 | 52 | 560 | 5.3 | 111 |

Referring to Table 1, the compounds of Synthesis Examples 1 to 5 exhibit a maximum absorption wavelength in a green wavelength region (e.g., 520 nm to 554 nm in a thin film state), a narrow full width at half maximum (FWHM), and a high absorption coefficient compared with the compounds of Comparative Synthesis Example 1 and Reference Synthesis Examples 1 and 2. Accordingly, the compounds of Synthesis Examples 1 to 5 exhibit excellent green wavelength selectivity and absorption intensity compared with the compounds of Comparative Synthesis Example 1 and Reference Synthesis Examples 1 and 2.

Example 1: Manufacture of Organic Photoelectric Device

Indium tin oxide (ITO) is sputtered on a glass substrate to form an about 150 nm-thick anode, and a 150 nm-thick active layer is formed thereon by codepositing the compound represented by Chemical Formula 1-1 according to Synthesis Example 1 (a p-type semiconductor compound) and C60 (an n-type semiconductor compound) in a thickness ratio of 1:1. On the active layer, a 10 nm-thick molybdenum oxide (MoOx, 0<x≤3) thin film is formed as a charge auxiliary layer. Subsequently, on the molybdenum oxide thin film, ITO is sputtered to form a 7 nm-thick cathode and thus manufacture an organic photoelectric device.

Examples 2 to 5: Manufacture of Organic Photoelectric Device

Each organic photoelectric device of Examples 2 to 5 is manufactured according to the same method as Example 1 except for respectively using the compounds of Synthesis Examples 2 to 5 instead of the compound of Synthesis Example 1.

Comparative Example 1: Manufacture of Organic Photoelectric Device

An organic photoelectric device of Comparative Example 1 is manufactured according to the same method as Example 1 except for using the compound of Comparative Synthesis Example 1 instead of the compound of Synthesis Example 1.

External Quantum Efficiency (EQE) of Organic Photoelectric Device

External quantum efficiency (EQE) of the organic photoelectric devices of Example 1 to 5 and Comparative Example 1 depending on a wavelength and a voltage is evaluated.

The external quantum efficiency is measured by using an IPCE measurement system (McScience Inc., Korea). First, the IPCE measurement system is calibrated by using a Si photodiode (Hamamatsu Photonics K.K., Japan) and then, respectively equipped on the organic photoelectric devices of Examples 1 to 5 and Comparative Example 1, and their external quantum efficiency at a wavelength ranging from about 350 to about 750 nm is measured. The results are shown in Table 2.

Color Reproducibility (ΔE*Ab) and Sensitivity (YSNR10) of Image Sensor

An image sensor is manufactured by respectively disposing the organic photoelectric devices of Examples 1 to 5 and Comparative Example 1 in a position of the organic photoelectric device 100 of the image sensor 300 shown in FIG. 4.

A minimum color difference ΔE*ab (a color difference between a reflected color and a transmitted color) of 24 colors of a Macbeth chart when a 18% gray patch of the Macbeth chart is taken a photograph of under D-65 of a standard light source. The color difference ΔE*ab is calculated according to Equation 1.

$$\Delta E = \sqrt{(\Delta L^*)^2 + (\Delta a^*)^2 + (\Delta b^*)^2}$$ [Equation 1]

In Equation 1,

ΔL* denotes a change of a color coordinate L* from the color coordinate L* at 23° C., Δa* denotes a change of a color coordinate a* from the color coordinate a* at 23° C., and Δb* denotes a change of a color coordinate b* from the color coordinate b* at 23° C.

Herein, lens having a F value of 2.8 and transmittance of 80% are used, and general interference-type lens are used as an infrared ray-cutting filter. The image sensor is set to have a pixel size of 1.4 μm and a frame rate of 15 fps.

TABLE 2

| Organic photoelectric device | EQE (%) (at −3 V) | Min. ΔE * ab |
|---|---|---|
| Example 1 | 68 | 3.5 |
| Example 2 | 62 | 2.5 |
| Example 3 | 76 | 3.9 |
| Example 4 | 74 | 3.0 |
| Example 5 | 74 | 3.0 |
| Comparative Example 1 | 60 | 4.0 |

As shown in Table 2, the organic photoelectric devices of Examples 1 to 5 exhibit excellent external quantum efficiency compared with the organic photoelectric device of Comparative Example 1. In addition, the organic photoelectric devices of Examples 1 to 5 exhibit a low minimum color difference ΔE*ab of less than or equal to 3.9 compared with the organic photoelectric devices of Comparative Example 1.

Sensitivity (YSNR10) of Image Sensor

YSNR10 of the image sensors of Examples 1, 2, 4, and 5 at ΔE*ab=3.5 is measured in a method described in Juha Alakarhu's "Image Sensors and Image Quality in Mobile Phones" in an outline collection of 2007 International Image Sensor Workshop (Ogunquit Me., USA).

The YSNR10 is obtained when a 18% gray patch of the Macbeth chart is taken a photograph of under a standard light source of D-65.

Herein, lens having a F value of 2.8 and transmittance of 80% is used, and interference-type lens are used as an infrared ray-cutting filter. The image sensors are set to have a pixel size of 1.4 μm and a frame rate of 15 fps.

The obtained colors are calibrated by using CCM (Color Correction Matrix), and the results are shown in Table 3.

TABLE 3

| Organic photoelectric device | YSNR10 (lux) (ΔE * ab = 3.5) |
|---|---|
| Example 1 | 80.7 |
| Example 2 | 85.6 |
| Example 4 | 78.1 |
| Example 5 | 77.8 |

Referring to Table 3, the image sensors respectively including the organic photoelectric devices of Examples 1, 2, 4, and 5 exhibit YSNR10 of less than or equal to 85.6 lux at ΔE*ab=3.5. Accordingly, the image sensors may have high sensitivity at a considerably high image quality pixel of 1.4 μm.

On the other hand, an image sensor including the organic photoelectric device of Comparative Example 1 may not have ΔE*ab=3.5, and thus its YSNR10 is impossible to calculate.

While this disclosure has been described in connection with what is presently considered to be practical example embodiments, it is to be understood that the inventive concepts are not limited to the disclosed embodiments, but, on the contrary, is intended to cover various modifications and equivalent arrangements included within the spirit and scope of the appended claims.

What is claimed is:

1. A compound represented by Chemical Formula 1:

[Chemical Formula 1]

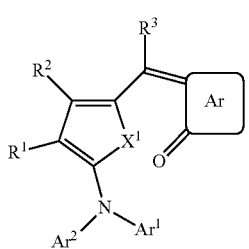

wherein, in Chemical Formula 1,
Ar is selected from a substituted or unsubstituted 5-membered aromatic ring, a substituted or unsubstituted 6-membered aromatic ring, and a condensed ring of two or more of the foregoing rings,
$X^1$ is Te, each of $R^1$ to $R^3$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, and
each of $Ar^1$ and $Ar^2$ are independently selected from a substituted or unsubstituted $C_6$ to $C_{30}$ aryl group, and a substituted or unsubstituted $C_3$ to $C_{30}$ heteroaryl group, provided that at least one of $Ar^1$ and $Ar^2$ is a heteroaryl group including at least one nitrogen (N) at an ortho position with respect to a bond with the nitrogen (N) of Chemical Formula 1.

2. The compound of claim 1, wherein, in Chemical Formula 1, at least one of $Ar^1$ and $Ar^2$ is selected from a substituted or unsubstituted pyrrolyl group, a substituted or unsubstituted prazolyl group, a substituted or unsubstituted midazolyl group, a substituted or unsubstituted oxazolyl group, a substituted or unsubstituted isoxazolyl group, a substituted or unsubstituted thiazolyl group, a substituted or unsubstituted isothiazolyl group, a substituted or unsubstituted pyridinyl group, a substituted or unsubstituted pyridazinyl group, a substituted or unsubstituted pyrimidinyl group, a substituted or unsubstituted pyrazinyl group, a substituted or unsubstituted indolyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, a substituted or unsubstituted pyridopyridazinyl group, a substituted or unsubstituted thienyl group, a substituted or unsubstituted benzothienyl group, a substituted or unsubstituted selenophenyl group, and a substituted or unsubstituted benzoselenophenyl group, and the functional groups may include at least one nitrogen (N) at an ortho position with respect to a bond with the nitrogen (N).

3. The compound of claim 1, wherein the compound represented by Chemical Formula 1 is represented by Chemical Formula 2:

[Chemical Formula 2]

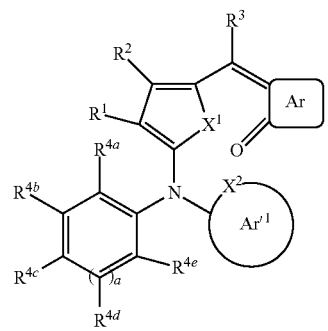

wherein, in Chemical Formula 2,
Ar is selected from a substituted or unsubstituted 5-membered aromatic ring, a substituted or unsubstituted 6-membered aromatic ring, and a condensed ring of two or more of the foregoing rings,
$X^1$ is Te, each of $R^1$ to $R^3$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof,
each of $R^{4a}$ to $R^{4e}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted C₃ to C₃₀ heteroaryl group, a halogen, a cyano group (—CN), a cyano-containing group, and a combination thereof, or optionally two adjacent groups of R⁴ᵃ to R⁴ᵉ are linked with each other to provide a 5-membered aromatic ring or a 6-membered aromatic ring, a is an integer of 0 or 1, X² is nitrogen (N), and Ar'¹ is heteroaryl group including at least one nitrogen (N) at an ortho position with respect to a bond with the nitrogen (N).

4. The compound of claim 3, wherein, in Chemical Formula 2, Ar'¹ is selected from a substituted or unsubstituted pyrrolyl group, a substituted or unsubstituted pyrazolyl group, a substituted or unsubstituted imidazolyl group, a substituted or unsubstituted oxazolyl group, a substituted or unsubstituted isoxazolyl group, a substituted or unsubstituted thiazolyl group, a substituted or unsubstituted isothiazolyl group, a substituted or unsubstituted pyridinyl group, a substituted or unsubstituted pyridazinyl group, a substituted or unsubstituted pyrimidinyl group, a substituted or unsubstituted pyrazinyl group, a substituted or unsubstituted indolyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, a substituted or unsubstituted pyridopyridazinyl group, a substituted or unsubstituted thienyl group, a substituted or unsubstituted benzothienyl group, a substituted or unsubstituted selenophenyl group, and a substituted or unsubstituted benzoselenophenyl group.

5. The compound of claim 1, wherein the compound represented by Chemical Formula 1 is represented by one of Chemical Formulae 3-1 to 3-6:

[Chemical Formula 3-1]

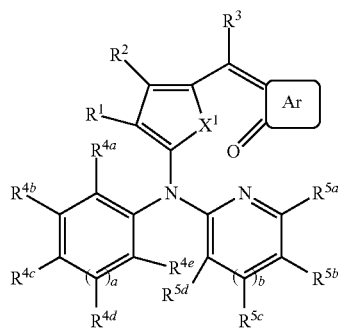

[Chemical Formula 3-2]

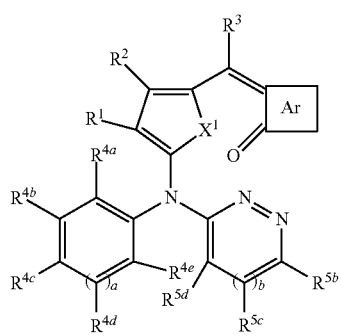

[Chemical Formula 3-3]

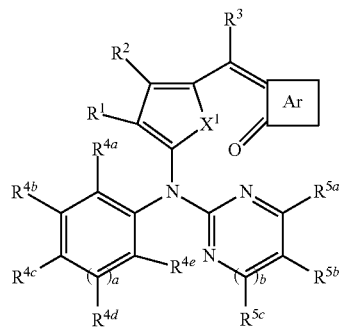

[Chemical Formula 3-4]

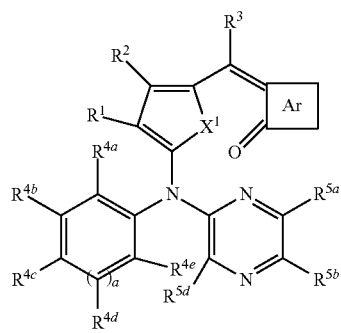

[Chemical Formula 3-5]

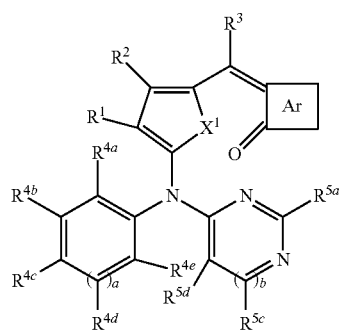

[Chemical Formula 3-6]

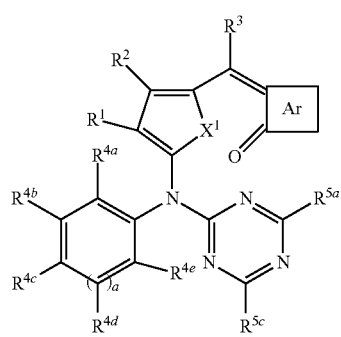

wherein, in Chemical Formulae 3-1 to 3-6,

Ar is selected from a substituted or unsubstituted 5-membered aromatic ring, a substituted or unsubstituted 6-membered aromatic ring, and a condensed ring of two or more of the foregoing rings, X¹ is Te, each of R¹ to R³ are independently selected from hydrogen, a substituted or unsubstituted C₁ to C₃₀ alkyl group, a substituted or unsubstituted C₁ to C₃₀ alkoxy group, a substituted or unsubstituted C₆ to C₃₀ aryl group, a substituted or unsubstituted C₃ to C₃₀ heteroaryl group, a halogen, a cyano group (—CN), a cyano-containing group, and a combination thereof, each of $R^{4a}$ to $R^{4e}$ or $R^{5a}$ to $R^{5d}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, or optionally two adjacent groups of $R^{4a}$ to $R^{4e}$ are linked with each other to provide a 5-membered aromatic ring or a 6-membered aromatic ring and optionally two adjacent groups of $R^{5a}$ to $R^{5d}$ are linked with each other to provide a 5-membered aromatic ring or a 6-membered aromatic ring, and each of a and b are independently an integer of 0 or 1.

6. The compound of claim 1, wherein a ring group represented by Ar and bound to a methine group is represented by Chemical Formula 4:

[Chemical Formula 4]

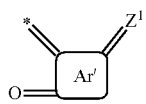

wherein, in Chemical Formula 4,

Ar' is selected from a substituted or unsubstituted 5-membered aromatic ring, a substituted or unsubstituted 6-membered aromatic ring, and a condensed ring of two or more of the foregoing rings, and $Z^1$ is O or $CR^bR^c$, wherein $R^b$ and $R^c$ are independently selected from hydrogen, a substituted or unsubstituted $C_1$ to $C_{10}$ alkyl group, a cyano group, or a cyano-containing group, provided that at least one of $R^b$ and $R^c$ is a cyano group or a cyano-containing group.

7. The compound of claim 1, wherein the ring group represented by Ar and bound to a methine group is a ring group represented by one of Chemical Formulae 5-1 to 5-4:

[Chemical Formula 5-1]

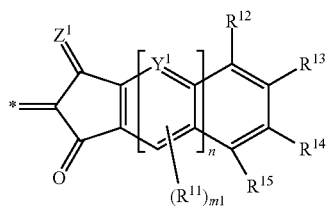

wherein, in Chemical Formula 5-1, $Z^1$ is O or $CR^bR^c$, wherein each of $R^b$ and $R^c$ are independently selected from hydrogen, a substituted or unsubstituted $C_1$ to $C_{10}$ alkyl group, a cyano group, or a cyano-containing group, provided that at least one of $R^b$ and $R^c$ is a cyano group or a cyano-containing group, $Y^1$ is selected from N and $CR^d$, wherein $R^d$ is selected from hydrogen and a substituted or unsubstituted $C_1$ to $C_{10}$ alkyl group, each of $R^{11}$, $R^{12}$, $R^{13}$, $R^{14}$, and $R^{15}$ are independently selected from hydrogen, a substituted or unsubstituted $C_1$ to $C_{30}$ alkyl group, a substituted or unsubstituted $C_6$ to $C_{30}$ aryl group, a substituted or unsubstituted C4 to $C_{30}$ heteroaryl group, a halogen, a cyano group (—CN), a cyano-containing group, and a combination thereof, or $R^{12}$ and $R^{13}$ are independently linked with each other and $R^{14}$ and $R^{15}$ are independently linked with each other to provide an aromatic ring, m1 is 0 or 1, and n is 0 or 1,

[Chemical Formula 5-2]

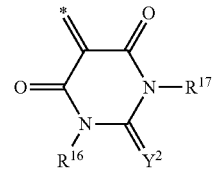

wherein, in Chemical Formula 5-2, $Y^2$ is selected from O, S, Se, Te, and $C(R^e)(CN)$ wherein $R^e$ is selected from hydrogen, a cyano group (—CN), and a $C_1$ to $C_{10}$ alkyl group, and each of $R^{16}$ and $R^{17}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_4$ to $C_{30}$ heteroaryl group, a halogen, a cyano group (—CN), and a combination thereof,

[Chemical Formula 5-3]

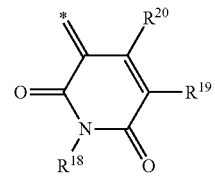

wherein, in Chemical Formula 5-3, each of $R^{18}$ to $R^{20}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted C4 to $C_{30}$ heteroaryl group, a halogen, a cyano group (—CN), a cyano-containing group, and a combination thereof,

[Chemical Formula 5-4]

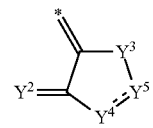

wherein, in Chemical Formula 5-4, $Y^2$ is selected from O, S, Se, Te, and $C(R^e)(CN)$ wherein $R^e$ is selected from hydrogen, a cyano group (—CN), and a $C_1$ to $C_{10}$ alkyl group, $Y^3$ is selected from O, S, Se, and Te, $Y^4$ is N or $NR^f$, $Y^5$ is selected from $CR^g$, C=O, C=S, $C=(CR^h)(CN)$, and Chemical Formula 5-4, at least one of $Y^2$ and $Y^5$ is C=O, each of $R^f$, $R^g$, and $R^h$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted C4 to $C_{30}$ heteroaryl group, a halogen, a cyano group (—CN), a cyano-containing group, and a combination thereof, and optionally $Y^4$ and $Y^5$ are linked with each other to provide a fused ring with a $Y^4$-$Y^5$-containing pentagonal ring of Chemical Formula 5-4.

8. The compound of claim 1, wherein the compound is represented by one of Chemical Formulae 6-1 to 6-4:

[Chemical Formula 6-1]

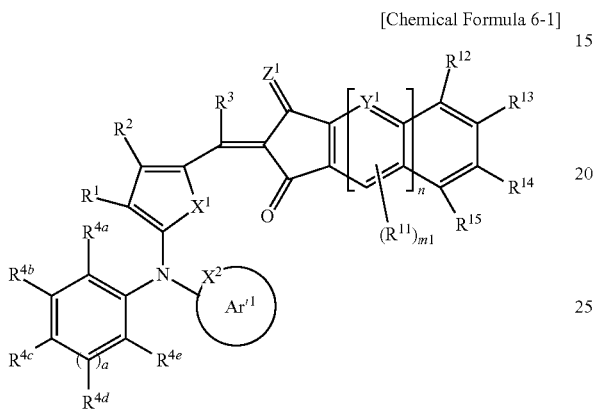

wherein, in Chemical Formula 6-1, $X^1$ is Te, each of $R^1$ to $R^3$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, $Z^1$ is O or $CR^bR^c$, wherein each of $R^b$ and $R^c$ are independently selected from hydrogen, a substituted or unsubstituted $C_1$ to $C_{10}$ alkyl group, a cyano group, or a cyano-containing group, provided that at least one of $R^b$ and $R^c$ is a cyano group or a cyano-containing group, $Y^1$ is selected from N and $CR^d$, wherein $R^d$ is selected from hydrogen and a substituted or unsubstituted $C_1$ to $C_{10}$ alkyl group, each of $R^{11}$, $R^{12}$, $R^{13}$, $R^{14}$, and $R^{15}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted C4 to $C_{30}$ heteroaryl group, a halogen, a cyano group (—CN), a cyano-containing group, and a combination thereof or $R^{12}$ and $R^{13}$ are independently linked with each other to provide an aromatic ring and $R^{14}$ and $R^{15}$ are independently linked with each other to provide an aromatic ring, m1 is 0 or 1, n is 0 or 1, each of $R^{4a}$ to $R^{4e}$ are independently selected from hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, or optionally two adjacent groups of $R^{4a}$ to $R^{4e}$ are linked with each other to provide a 5-membered aromatic ring or a 6-membered aromatic ring, a is an integer of 0 or 1, $X^2$ is nitrogen (N), and $Ar'^1$ is a heteroaryl group including at least one nitrogen (N) at an ortho position with respect to a bond with the nitrogen (N),

[Chemical Formula 6-2]

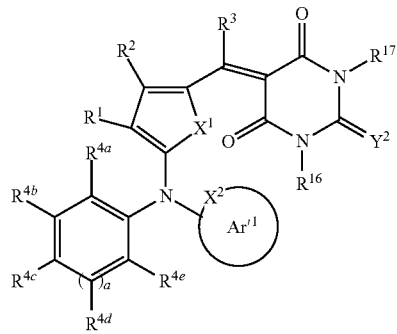

wherein, in Chemical Formula 6-2, $X^1$ is Te, $Y^2$ is selected from O, S, Se, Te, and $C(R^e)(CN)$ wherein $R^e$ is selected from hydrogen, a cyano group (—CN), and a $C_1$ to $C_{10}$ alkyl group, each of $R^1$, $R^2$, $R^3$, $R^{16}$, and $R^{17}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted C4 to $C_{30}$ heteroaryl group, a halogen, a cyano group (—CN), a cyano-containing group, and a combination thereof, each of $R^{4a}$ to $R^{4e}$ are independently selected from hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, or optionally two adjacent groups of $R^{4a}$ to $R^{4e}$ are linked with each other to provide a 5-membered aromatic ring or a 6-membered aromatic ring, a is an integer of 0 or 1, $X^2$ is nitrogen (N), and $Ar'^1$ is a heteroaryl group including at least one nitrogen (N) at an ortho position with respect to a bond with the nitrogen (N),

[Chemical Formula 6-3]

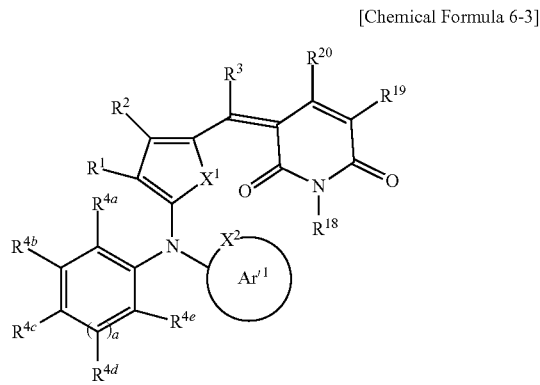

wherein, in Chemical Formula 6-3,
$X^1$ is Te, each of $R^1$, $R^2$, $R^3$, $R^{18}$, $R^{19}$, and $R^{20}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted C4 to $C_{30}$ heteroaryl group, a halogen, a cyano group (—CN), a cyano-containing group, and a combination thereof,
$R^{4a}$ to $R^{4e}$ are independently selected from hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, or optionally two adjacent groups of $R^{4a}$ to $R^{4e}$ are linked with each other to provide a 5-membered aromatic ring or a 6-membered aromatic ring,
a is an integer of 0 or 1,
$X^2$ is nitrogen (N), and
$Ar'^1$ is a heteroaryl group including at least one nitrogen (N) at an ortho position with respect to a bond with the nitrogen (N),

[Chemical Formula 6-4]

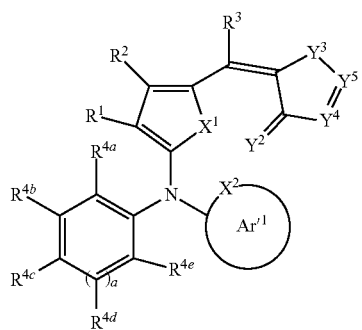

wherein, in Chemical Formula 6-4,
$X^1$ is Te, $Y^2$ is selected from O, S, Se, Te, and $C(R^e)(CN)$ wherein $R^e$ is selected from hydrogen, a cyano group (—CN), and a $C_1$ to $C_{10}$ alkyl group,
$Y^3$ is selected from O, S, Se, and Te,
$Y^4$ is N or $NR^f$,
$Y^5$ is selected from $CR^g$, C=O, C=S, $C=(CR^h)(CN)$, and Chemical Formula 5-4,
at least one of $Y^2$ and $Y^5$ is C=O,
each of $R^1$, $R^2$, $R^3$, $R^f$, $R^g$, and $R^h$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted C4 to $C_{30}$ heteroaryl group, a halogen, a cyano group (—CN), a cyano-containing group, and a combination thereof,
optionally $Y^4$ and $Y^5$ are linked with each other to provide a fused ring with a $Y^4$-$Y^5$-containing pentagonal ring of Chemical Formula 5-4,
each of $R^{4a}$ to $R^{4e}$ are independently selected from hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, or optionally two adjacent groups of $R^{4a}$ to $R^{4e}$ are linked with each other to provide a 5-membered aromatic ring or a 6-membered aromatic ring,
a is an integer of 0 or 1,
$X^2$ is nitrogen (N), and
$Ar'^1$ is a heteroaryl group including at least one nitrogen (N) at an ortho position with respect to a bond with nitrogen (N).

9. The compound of claim 1, wherein the compound has a maximum absorption wavelength ($\lambda_{max}$) in a wavelength region of greater than or equal to about 510 nm and less than about 560 nm.

10. The compound of claim 1, wherein the compound has a maximum absorption wavelength ($\lambda_{max}$) in a wavelength region of about 520 nm to about 555 nm in a thin film state.

11. The compound of claim 1, wherein the compound exhibits a light absorption curve having a full width at half maximum (FWHM) of about 50 nm to about 110 nm, in a thin film state.

12. An organic photoelectric device, comprising:
a first electrode and a second electrode facing each other, and
an active layer between the first electrode and the second electrode, the active layer including a compound represented by Chemical Formula 1:

[Chemical Formula 1]

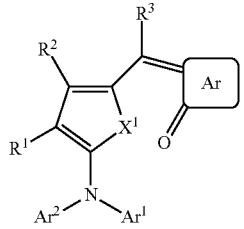

wherein, in Chemical Formula 1,
Ar is selected from a substituted or unsubstituted 5-membered aromatic ring, a substituted or unsubstituted 6-membered aromatic ring, and a condensed ring of two or more of the foregoing rings,
$X^1$ is Te, each of $R^1$ to $R^3$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, and
each of $Ar^1$ and $Ar^2$ are independently selected from a substituted or unsubstituted $C_6$ to $C_{30}$ aryl group, and a substituted or unsubstituted $C_3$ to $C_{30}$ heteroaryl group, provided that at least one of $Ar^1$ and $Ar^2$ is a heteroaryl group including at least one nitrogen (N) at an ortho position with respect to a linking group with the nitrogen (N).

13. The organic photoelectric device of claim 12, wherein, in Chemical Formula 1, at least one of $Ar^1$ and $Ar^2$ is selected from a substituted or unsubstituted pyrrolyl group, a substituted or unsubstituted prazolyl group, a substituted or unsubstituted midazolyl group, a substituted or unsubstituted oxazolyl group, a substituted or unsubstituted isoxazolyl group, a substituted or unsubstituted thiazolyl group, a substituted or unsubstituted isothiazolyl group, a substituted or unsubstituted pyridinyl group, a substituted or unsubstituted pyridazinyl group, a substituted or unsubstituted pyrimidinyl group, a substituted or unsubstituted pyrazinyl group, a substituted or unsubstituted indolyl group, a substituted or unsubstituted a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, a substituted or unsubstituted pyridopyridazinyl group, a substituted or unsubstituted thienyl group, a substituted or unsubstituted benzothienyl group, a substituted or unsubstituted selenophenyl group, and a substituted or unsubstituted benzoselenophenyl group, and the functional groups may include at least one nitrogen (N) at an ortho position with respect to a bond with the nitrogen (N).

14. The organic photoelectric device of claim 12, wherein the compound represented by Chemical Formula 1 is represented by Chemical Formula 2:

[Chemical Formula 2]

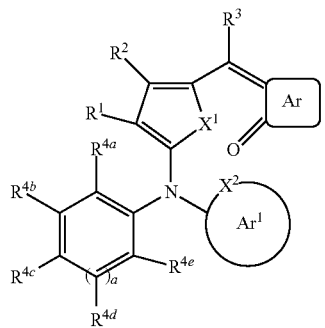

wherein, in Chemical Formula 2,
Ar is selected from a substituted or unsubstituted 5-membered aromatic ring, a substituted or unsubstituted 6-membered aromatic ring, and a condensed ring of two or more of the foregoing rings,
$X^1$ is Te, each of $R^1$ to $R^3$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof,
each of $R^{4a}$ to $R^{4e}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, or optionally two adjacent groups of $R^{4a}$ to $R^{4e}$ are linked with each other to provide a 5-membered aromatic ring or a 6-membered aromatic ring,
a is an integer of 0 or 1,
$X^2$ is nitrogen (N), and
$Ar^1$ is a heteroaryl group including at least one nitrogen (N) at an ortho position with respect to a bond with the nitrogen (N).

15. The organic photoelectric device of claim 14, wherein, in Chemical Formula 2, $Ar^1$ is selected from a substituted or unsubstituted pyrrolyl group, a substituted or unsubstituted pyrazolyl group, a substituted or unsubstituted imidazolyl group, a substituted or unsubstituted oxazolyl group, a substituted or unsubstituted isoxazolyl group, a substituted or unsubstituted thiazolyl group, a substituted or unsubstituted isothiazolyl group, a substituted or unsubstituted pyridinyl group, a substituted or unsubstituted pyridazinyl group, a substituted or unsubstituted pyrimidinyl group, a substituted or unsubstituted pyrazinyl group, a substituted or unsubstituted indolyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, a substituted or unsubstituted pyridopyridazinyl group, a substituted or unsubstituted thienyl group, a substituted or unsubstituted benzothienyl group, a substituted or unsubstituted selenophenyl group, and a substituted or unsubstituted benzoselenophenyl group.

16. The organic photoelectric device of claim 12, wherein the compound represented by Chemical Formula 1 is represented by Chemical Formula 3:

[Chemical Formula 3]

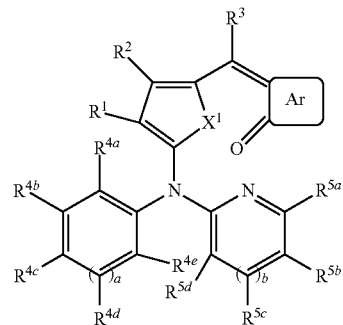

wherein, in Chemical Formula 3,
Ar is selected from a substituted or unsubstituted 5-membered aromatic ring, a substituted or unsubstituted 6-membered aromatic ring, and a condensed ring of two or more of the foregoing rings,
$X^1$ is Te, each of $R^1$ to $R^3$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof,
each of $R^{4a}$ to $R^{4e}$ or $R^{5a}$ to $R^{5d}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, or optionally two adjacent groups of $R^{4a}$ to $R^{4e}$ are linked with each other to provide a 5-membered aromatic ring or a 6-membered aromatic ring and optionally two adjacent groups of $R^{5a}$ to $R^{5d}$ are linked with each other to provide a 5-membered aromatic ring or a 6-membered aromatic ring, and
each of a and b are independently an integer of 0 or 1.

17. The organic photoelectric device of claim 12, wherein, in Chemical Formula 1, a ring group represented by Ar and bound to a methine group is represented by Chemical Formula 4:

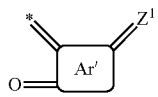

[Chemical Formula 4]

wherein, in Chemical Formula 4,

Ar' is selected from a substituted or unsubstituted 5-membered aromatic ring, a substituted or unsubstituted 6-membered aromatic ring, and a condensed ring of two or more of the foregoing rings, $Z^1$ is a or $CR^bR^c$, wherein each of $R^b$ and $R^c$ are independently selected from hydrogen, a substituted or unsubstituted $C_1$ to $C_{10}$ alkyl group, a cyano group, or a cyano-containing group, provided that at least one of $R^b$ and $R^c$ is a cyano group or a cyano-containing group.

18. The organic photoelectric device of claim 12, wherein a ring group represented by Ar and bound to a methine group is a cyclic group represented by one of Chemical Formulae 5-1 to 5-4:

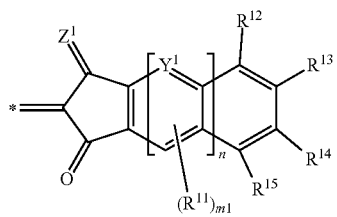

[Chemical Formula 5-1]

wherein, in Chemical Formula 5-1, $Z^1$ is O or $CR^bR^c$, wherein each of $R^b$ and $R^c$ are independently selected from hydrogen, a substituted or unsubstituted $C_1$ to $C_{10}$ alkyl group, a cyano group, or a cyano-containing group, provided that at least one of $R^b$ and $R^c$ is a cyano group or a cyano-containing group, $Y^1$ is selected from N and $CR^d$, wherein $R^d$ is selected from hydrogen and a substituted or unsubstituted $C_1$ to $C_{10}$ alkyl group, each of $R^{11}$, $R^{12}$, $R^{13}$, $R^{14}$, and $R^{15}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_4$ to $C_{30}$ heteroaryl group, a halogen, a cyano group (—CN), a cyano-containing group, and a combination thereof, or $R^{12}$ and $R^{13}$ are independently linked with each other to provide an aromatic ring and $R^{14}$ and $R^{15}$ are independently linked with each other to provide an aromatic ring, m1 is 0 or 1, and
n is 0 or 1,

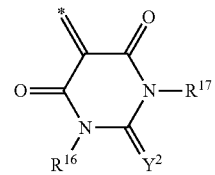

[Chemical Formula 5-2]

wherein, in Chemical Formula 5-2, $Y^2$ is selected from O, S, Se, Te, and $C(R^e)(CN)$ wherein $R^e$ is selected from hydrogen, a cyano group (—CN), and a $C_1$ to $C_{10}$ alkyl group, and each of $R^{16}$ and $R^{17}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted C4 to $C_{30}$ heteroaryl group, a halogen, a cyano group (—CN), and a combination thereof,

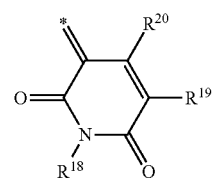

[Chemical Formula 5-3]

wherein, in Chemical Formula 5-3, each of $R^{18}$ to $R^{20}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted C4 to $C_{30}$ heteroaryl group, a halogen, a cyano group (—CN), a cyano-containing group, and a combination thereof,

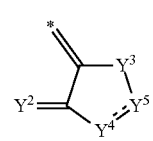

[Chemical Formula 5-4]

wherein, in Chemical Formula 5-4, $Y^3$ is selected from O, S, Se, and Te,
$Y^4$ is N or $NR^f$,
$Y^5$ is selected from $CR^g$, C=O, C=S, $C=(CR^h)(CN)$, and Chemical Formula 5-4, at least one of $Y^2$ and $Y^5$ is C=O, each of $R^f$, $R^g$ and $R^h$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted C4 to $C_{30}$ heteroaryl group, a halogen, a cyano group (—CN), a cyano-containing group, and a combination thereof, and optionally $Y^4$ and $Y^5$ are linked with each other to provide a fused ring with a $Y^4$-$Y^5$-containing pentagonal ring of Chemical Formula 5-4.

19. The organic photoelectric device of claim 12, wherein the compound represented by Chemical Formula 1 is a compound represented by one of Chemical Formulae 6-1 to 6-4:

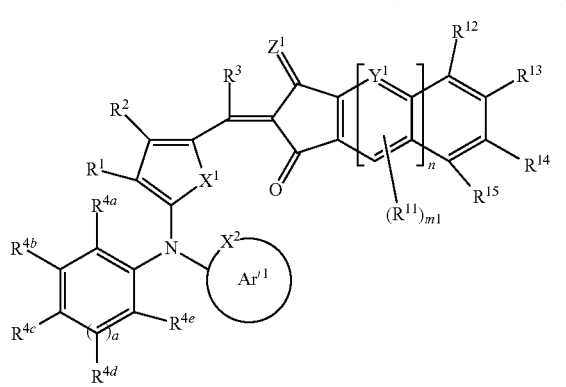

[Chemical Formula 6-1]

wherein, in Chemical Formula 6-1, $X^1$ is Te, each of $R^1$ to $R^3$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, $Z^1$ is O or $CR^bR^c$, wherein $R^b$ and $R^c$ are independently selected from hydrogen, a substituted or unsubstituted $C_1$ to $C_{10}$ alkyl group, a cyano group, or a cyano-containing group, provided that at least one of $R^b$ and $R^c$ is a cyano group or a cyano-containing group, $Y^1$ is selected from N and $CR^d$, wherein $R^d$ is selected from hydrogen and a substituted or unsubstituted $C_1$ to $C_{10}$ alkyl group, each of $R^{11}$, $R^{12}$, $R^{13}$, $R^{14}$, and $R^{15}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted C4 to $C_{30}$ heteroaryl group, a halogen, a cyano group (—CN), a cyano-containing group, and a combination thereof or $R^{12}$ and $R^{13}$ are independently linked with each other to provide an aromatic ring and $R^{14}$ and $R^{15}$ are independently linked with each other to provide an aromatic ring, m1 is 0 or 1, n is 0 or 1, each of $R^{4a}$ to $R^{4e}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, or optionally two adjacent groups of $R^{4a}$ to $R^{4e}$ are linked with each other to provide a 5-membered aromatic ring or a 6-membered aromatic ring, and a is an integer of 0 or 1,

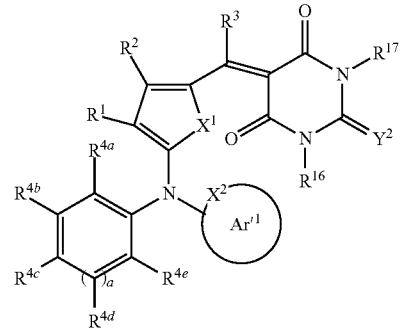

[Chemical Formula 6-2]

wherein, in Chemical Formula 6-2, $X^1$ is Te, $Y^2$ is selected from O, S, Se, Te, and $C(R^e)(CN)$ wherein $R^e$ is selected from hydrogen, a cyano group (—CN), and a $C_1$ to $C_{10}$ alkyl group, each of $R^1$, $R^2$, $R^3$, $R^{16}$, and $R^{17}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted C4 to $C_{30}$ heteroaryl group, a halogen, a cyano group (—CN), a cyano-containing group, and a combination thereof, each of $R^{4a}$ to $R^{4e}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, or optionally two adjacent groups of $R^{4a}$ to $R^{4e}$ are linked with each other to provide a 5-membered aromatic ring or a 6-membered aromatic ring, and a is an integer of 0 or 1,

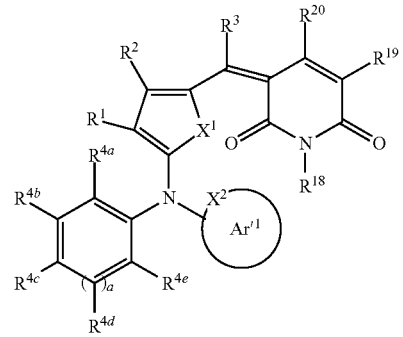

[Chemical Formula 6-3]

wherein, in Chemical Formula 6-3, $X^1$ is Te, each of $R^1$, $R^2$, $R^3$, $R^{18}$, $R^{19}$, and $R^{20}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted C4 to $C_{30}$ heteroaryl group, a halogen, a cyano group (—CN), a cyano-containing group, and a combination thereof, each of $R^{4a}$ to $R^{4e}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, or optionally two adjacent groups of $R^{4a}$ to $R^{4e}$ are linked with each other to provide a 5-membered aromatic ring or a 6-membered aromatic ring, and a is an integer of 0 or 1,

[Chemical Formula 6-4]

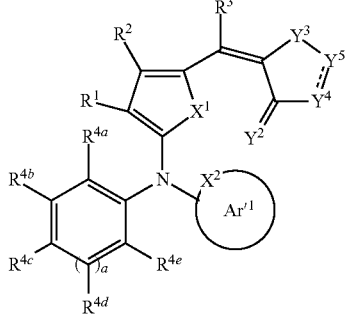

wherein, in Chemical Formula 6-4, $X^1$ is Te, $Y^2$ is selected from O, S, Se, Te, and $C(R^e)(CN)$ wherein $R^e$ is selected from hydrogen, a cyano group (—CN), and a $C_1$ to $C_{10}$ alkyl group, $Y^3$ is selected from O, S, Se, and Te, $Y^4$ is N or $NR^f$, $Y^5$ is selected from $CR^g$, C=O, C=S, C=$(CR^h)$(CN), and Chemical Formula 5-4, at least one of $Y^2$ and $Y^5$ is C=O, each of $R^1$, $R^2$, $R^3$, $R^f$, $R^g$, and $R^h$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted C4 to $C_{30}$ heteroaryl group, a halogen, a cyano group (—CN), a cyano-containing group, and a combination thereof, optionally $Y^4$ and $Y^5$ are linked with each other to provide a fused ring with a $Y^4$-$Y^5$-containing pentagonal ring of Chemical Formula 5-4, each of $R^{4a}$ to $R^{4e}$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof, or optionally two adjacent groups of $R^{4a}$ to $R^{4e}$ are linked with each other to provide a 5-membered aromatic ring or a 6-membered aromatic ring, and a is an integer of 0 or 1,

[Chemical Formula 5-4]

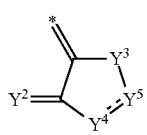

wherein, in Chemical Formula 5-4, $Y^3$ is selected from O, S, Se, and Te, $Y^4$ is N or $NR^f$, $Y^5$ is selected from $CR^g$, C=O, C=S, C=$(CR^h)$(CN), and Chemical Formula 5-4, at least one of $Y^2$ and $Y^5$ is C=O, each of $R^f$, $R^g$, and $R^h$ are independently selected from hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted C4 to $C_{30}$ heteroaryl group, a halogen, a cyano group (—CN), a cyano-containing group, and a combination thereof, and optionally $Y^4$ and $Y^5$ are linked with each other to provide a fused ring with a $Y^4$-$Y^5$-containing pentagonal ring of Chemical Formula 5-4.

20. The organic photoelectric device of claim 12, wherein the active layer has a maximum absorption wavelength ($\lambda_{max}$) in a wavelength region of greater than or equal to about 510 nm and less than about 560 nm.

21. The organic photoelectric device of claim 12, wherein the active layer has a maximum absorption wavelength ($\lambda_{max}$) in a wavelength region of about 520 nm to about 555 nm.

22. The organic photoelectric device of claim 12, wherein the active layer exhibits a light absorption curve having a full width at half maximum (FWHM) of about 50 nm to about 110 nm.

23. The organic photoelectric device of claim 12, wherein the active layer has have an absorption coefficient of greater than or equal to about $5.5 \times 10^4$ cm$^{-1}$, when including the compound represented by Chemical Formula 1 and C60 in a volume ratio of about 0.9:1 to about 1.1:1.

24. The organic photoelectric device of claim 12, wherein the active layer has have an absorption coefficient of about $5.8 \times 10^4$ cm$^{-1}$ to about $10 \times 10^4$ cm$^{-1}$, when including the compound represented by Chemical Formula 1 and C60 in a volume ratio of about 0.9:1 to about 1.1:1.

25. An image sensor comprising the organic photoelectric device of claim 12.

26. The image sensor of claim 25, wherein the image sensor includes a semiconductor substrate integrated with a plurality of first photo-sensing devices sensing light in a blue wavelength region and a plurality of second photo-sensing devices sensing light in a red wavelength region, and the organic photoelectric device on the semiconductor substrate and selectively sensing light in a green wavelength region.

27. The image sensor of claim 26, wherein the image sensor further includes a color filter layer between the semiconductor substrate and the organic photoelectric device, and including a blue filter selectively absorbing light in a blue wavelength region and a red filter selectively absorbing light in a red wavelength region.

28. The image sensor of claim 26, wherein the plurality of first photo-sensing devices and the plurality of second photo-sensing devices are stacked in a vertical direction in the semiconductor substrate.

29. The image sensor of claim 25, wherein the image sensor includes a green photoelectric device of the organic photoelectric device, a blue photoelectric device selectively absorbing light in a blue wavelength region, and a red photoelectric device selectively absorbing light in a red wavelength region that are stacked.

30. The image sensor of claim 25, wherein the image sensor has a color difference ($\Delta E^*ab$) of less than about 4.0.

31. An electronic device comprising the image sensor of claim 25.

\* \* \* \* \*